US008697747B2

(12) United States Patent
Nielsen et al.

(10) Patent No.: US 8,697,747 B2
(45) Date of Patent: Apr. 15, 2014

(54) ENHANCING COAGULATION OR REDUCING FIBRINOLYSIS

(75) Inventors: Vance G. Nielsen, Moorestown, NJ (US); James F. George, Birmingham, AL (US); James K. Kirklin, Birmingham, AL (US)

(73) Assignee: THe UAB Research Foundation, Birmingham, AL (US)

( * ) Notice: Subject to any disclaimer, the term of this patent is extended or adjusted under 35 U.S.C. 154(b) by 0 days.

(21) Appl. No.: 13/254,287

(22) PCT Filed: Mar. 5, 2010

(86) PCT No.: PCT/US2010/026377
§ 371 (c)(1),
(2), (4) Date: Sep. 22, 2011

(87) PCT Pub. No.: WO2010/102216
PCT Pub. Date: Sep. 10, 2010

(65) Prior Publication Data
US 2012/0045518 A1    Feb. 23, 2012

Related U.S. Application Data

(60) Provisional application No. 61/157,719, filed on Mar. 5, 2009.

(51) Int. Cl.
*A01N 55/02*     (2006.01)
(52) U.S. Cl.
USPC .......................................... 514/492; 514/724
(58) Field of Classification Search
None
See application file for complete search history.

(56) References Cited

U.S. PATENT DOCUMENTS 7,045,140 B2    5/2006    Motterlini et al.

FOREIGN PATENT DOCUMENTS

| WO | 02/092075 | 11/2002 |
|---|---|---|
| WO | 2004/043341 | 5/2004 |
| WO | 2004/045598 | 6/2004 |
| WO | 2004/045599 | 6/2004 |
| WO | 2005/013691 | 2/2005 |
| WO | 2005/114161 | 12/2005 |
| WO | 2007/085806 | 8/2007 |
| WO | 2008/003953 | 1/2008 |

OTHER PUBLICATIONS

Dahlback, "Blood Coagulation" (2000), Lancet, vol. 355, 1627-1632.*
Levi and Cate, "Disseminated Intravascular Coagulation" (1999), New England Journal of Medicine, vol. 341, 586-591.*
Extended European Search Report for EP 10749399.1; mailed Jun. 1, 2012; 7 pages.
Axon et al., "PentaLyte decreases lung injury after aortic occlusion-reperfusion," Am J Respir Crit Care Med, 157: 1982-1990 (1998).
Brune et al., "Activation of soluble guanylate cyclase by carbon monoxide and inhibition by superoxide anion," Eur J. Biochem., 192: 683-688 (1990).
Brune et al., "Inhibition of platelet aggregation by carbon monoxide is mediated by activation of guanylate cyclase," Mol Pharmacol 32(4): 497-504 (1987).
Carr et al., "Effect of fibrin structure on plasmin-mediated dissolution of plasma clots," Blood Coagul Fibrinolysis, 6:567-573 (1995).
Chlopicki et al., "Carbon monoxide released by CORM-3 inhibits human platelets by a mechanism independent of soluble guanylate cyclase," Cardiovascular Research, 71: 393-401 (2006).
De Pietri et al., "Use of recombinant factor IX and thrombelastography in a patient with hemophilia B undergoing liver transplantation: a case report," Transplant Proc., 40:2007-2009 (2008).
Dehmel et al., "Thrombelastographic monitoring of recombinant factor VIIa in acquired haemophilia," Haemophilia, 14: 736-742 (2008).
Dong et al., "Tricarbonyldichlororuthenium (II) dimer (CORM2) activates non-selective cation current in human endothelial cells independently of carbon monoxide releasing," Eur J Pharmacol, 590: 99-104 (2008).
Fries et al., "Effect of fibrinogen on reversal of diluational coagulopathy: a porcine model," Br J Anaesth, 95:172-177 (2005).
Fries et al., "Time for changing coagulation management in trauma-related massive bleeding," Curr Opin Anaesthesiol, 22: 267-274 (2009).
Guillen et al., "The CO-releasing molecule CORM-2 is a novel regulator of the inflammatory process in osteoarthritic chondrocytes," Rheumatology, 47(9): 1323-1328 (2008).
Guo et al., "Administration of a CO-releasing molecule at the time of reperfusion reduces infarct size in vivo," Am J Physiol Heart Circ Physiol 286: H1649-H1653 (2004).
Hardy et al., "Massive transfusion and coagulopathy: pathophysiology and implications for clinical management," Can J Anaesth, 53: S40:S58 (2006).
Johansen et al., "Acquired haemophilia: dynamic whole blood coagulation utilized to guide haemostatic therapy," Haemophilia, 12:190-197 (2006).
Kheirabadi et al., "Effects of synthetic versus natural colloid resuscitation on inducing dilutional coagulopathy and increasing hemorrhage in rabbits," J. Trauma, 64:1218-1229 (2008).
Kheirabadi et al., "In vivo bleeding time and in vitro thrombelastography measurements are better indicators of dilutional hypothermic coagulopathy than prothrombin time," J. Trauma, 62:1352-1361 (2007).

(Continued)

*Primary Examiner* — Jon P Weber
*Assistant Examiner* — Teresa E Knight
(74) *Attorney, Agent, or Firm* — Kilpatrick Townsend & Stockton LLP

(57) ABSTRACT

Methods for controlling bleeding (e.g., enhancing coagulation and reducing fibrinolysis) in a subject are disclosed. The methods include selecting a subject in need of enhanced coagulation or reduced fibrinolysis, and administering to the subject a carbon monoxide releasing molecule (CORM). Examples of CORMs include tricarbonyldichloro-ruthenium (II) dimer, tricarbonylchloro-(glycinato)ruthenium (II), sodium boranocarbonate, dimanganese decacarbonyl, and iron pentacarbonyl. Further disclosed are compositions and methods for treating a subject in need of a blood product by administering to the subject a composition including a CORM and a blood product (e.g., cryoprecipitate or fresh frozen plasma).

16 Claims, 23 Drawing Sheets

(56) References Cited

OTHER PUBLICATIONS

Masini et al., "A carbon monoxide-releasing molecule (CORM-3) abrogates polymorphonuclear granulocyte-induced activation of endothelial cells and mast cells," The FASEB Journal, 22: 3380-3388 (2008).
Megias et al., "The carbon monoxide-releasing molecule CORM-2 inhibits the inflammatory response induced by cytokines in Caco-2 cells," Br J Pharm, 150:977-986 (2007).
Mosesson, M.W., "Fibrinogen and fibrin structure and functions," J. Thromb. Haemostat., 3:1894-1904 (2005).
Motterlini et al., "Carbon monoxide-releasing molecules (CO-RMs): vasodilatory, antiischaemic and anti-inflammatory activites," Biochem Soc Trans, 35:1142-1146 (2007).
Motterlini et al., "Carbon monoxide-releasing molecules: characterization of biochemical and vascular activities," Circ. Res., 90:e17-e24 (2002).
Motterlini et al., "CORM-A1: a new pharmacologically active carbon monoxide-releasing molecule," The FASEB Journal, 19, 2004.
Motterlini et al., "Therapeutic applications of carbon monoxide-releasing molecules," Expert Opin Investig Drugs, 14:1305-1318 (2005).
Nielsen et al., "Carbon monoxide releasing molecule-2 decreases fibrinolysis in human plasma," Blood Coagul Fibrinolysis, 20(6): 448-455 (2009).
Nielsen et al., "Carbon Monoxide Releasing Molecule-2 Decreases Thick Diameter Fibrin Fiber Formation in Normal and Factor XIII Deficient Plasmas," Blood Coagul Fibrinolysis, 21(1): 101-105 (2010).
Nielsen et al., "Carbon Monoxide Releasing Molecule-2 Enhances Coagulation and Diminishes Fibrinolytic Vulnerability in Diluted Plasma in vitro," J. Trauma, 70(4): 1-9 (2010).
Nielsen et al., "Carbon Monoxide Releasing Molecule-2 Enhances Coagulation and Diminishes Fibrinolytic Vulnerability in Subjects Exposed to Warfarin," Thromb Res., 126(1): 68-73 (2010).
Nielsen et al., "Carbon Monoxide Releasing Molecule-2 Enhances Coagulation in Rat and Rabbit Plasma," Blood Coagul Fibrinolysis, 21(3): 298-299 (2010).
Nielsen et al., "Carbon Monoxide Releasing Molecule-2 Increases Fibrinogen-Dependent Coagulation Kinetics But Does Not Enhance Prothrombin Activity," Blood Coagul Fibrinolysis, 21(4): 349-353 (2010).
Nielsen et al., "Carbon monoxide releasing molecule-2 increases the velocity of thrombus growth and strength in hemophilia A, hemophilia B and factor VII deficient plasmas," Blood Coagul Fibrinolysis, 21(1): 41-45 (2010).
Nielsen et al., "Carbon monoxide releasing molecule-2 increases the velocity of thrombus growth and strength in human plasma," Blood Coagul Fibrinolysis, 20(5): 377-80 (2009).
Nielsen et al., "Effects of coagulation factor deficiency on plasma coagulation kinetics determined via Thrombelastography®: critical roles of fibrinogen and Factors II, VII, X, and XII," Acta Anaesthesiol Scand, 49:222-231 (2005).
Nielsen et al., "Elastic modulus-based thrombelastographic quantification of plasma clot fibrinolysis with progressive plasminogen activation," Blood Coagul Fibrinolysis, 17:75-81 (2006).
Nielsen et al., "Hextend (hetastarch solution) decreases multiple organ injury and xanthine oxidase release after hepatoenteric ischemia-reperfusion in rabbits," Crit Care Med, 25: 1565-1574 (1997).
Nielsen et al., "Qualitative thrombelastographic detection of tissue factor in human plasma," Anesth Analg, 104: 59-64 (2007).
Nielsen et al., "The Impact of Factor XIII on Coagulation Kinetics and Clot Strength Determined by Thrombelastography," Anesth Analg 99(1): 120-123 (2004).
Nielsen, V.G., "Colloids decrease clot propagation and strength: role of factor XIII-fibrin polymer and thrombin-fibrinogen interactions," Acta Anaesthesiol Scand, 49:1163-1171 (2005).
Nielsen, V.G., "Corn trypsin inhibitor decreases tissue-type plasminogen activator-mediated fibrinolysis of human plasma," Blood Coagul Fibrinolysis, 20(3): 191-196 (2009).
Nielsen, V.G., "Effects of PentaLyte and Voluven hemodilution on plasma coagulation kinetics in the rabbit: role of thrombin-fibrinogen and factor XIII-fibrin interactions," Acta Anaesthesiol Scand, 49: 1263-1271 (2005).
Nielsen, V.G., "Hemodilution modulates the time of onset and rate of fibrinolysis in human and rabbit plasma," J Heart Lung Transplant, 25: 1344-1352 (2006).
Nielsen, V.G., "Hydroxyethyl starch enhances fibrinolysis in human plasma by diminishing $\alpha 2$-antiplasmin-plasmin interactions," Blood Coagul Fibrinolysis, 18: 647-656 (2007).
Pivalizza et al., "Thrombelastography-guided factor VIIa therapy in a surgical patient with severe hemophilia and factor VIII inhibitor," Anesth Analg, 107: 398-401 (2008).
Sun et al., "Carbon monoxide releasing molecules: New insights for anticoagulation strategy in sepsis," Cellular and Molecular Life Sciences, 66: 365-369 (2009).
Sun et al., "CO-releasing molecules (CORM-2)-liberated CO attenuates leukocytes infiltration in the renal tissue of thermally injured mice," Int. J. Biol. Sci., 4(3): 176-183 (2008).
True et al., "Heme Oxygenase-1 Deficiency Accelerates Formation of Arterial Thrombosis Through Oxidative Damage to the Endothelium, Which Is Rescued by Inhaled Carbon Monoxide," Circulation Research 101:893-901 (2007).
Wettstein et al., "Decreased factor XIII availability for thrombin and early loss of clot firmness in patients with unexplained intraoperative bleeding," Anesth. Analg., 99:1564-1569 (2004).
Wu et al., "Carbon monoxide: endogenous production, physiological functions, and pharmacological applications," Pharmacol Rev., 57:585-630 (2005).
Young et al., "Evaluation of thromboelastography for monitoring recombinant activated factor VII ex vivo in haemophilia A and B patients with inhibitors: a multicentre trial," Blood Coagul Fibrinolysis, 19:276-282 (2008).
Young et al., "Individualization of bypassing agent treatment for haemophilic patients with inhibitors utilizing thromboelastography," Haemophilia, 12:598-604 (2006).
Arkebauer et al., "Carbon monoxide and nitric oxide modulate $\alpha 2$-antiplasmin and plasmin activity: role of heme," Blood Coagulation and Fibrinolysis, 22 (2011), 712-719.
Cohen et al., "Carbon monoxide releasing molecule-2 enhances coagulation and attenuates fibrinolysis by two mechanisms: insights gained with colloid dilution," Blood Coagulation and Fibrinolysis, 22:60-66 (2011).
Nielsen et al., "Carbon monoxide-releasing molecule-2 enhances coagulation in rabbit plasma and decreases bleeding time in clopidogrel/aspirin-treated rabbits," Blood Coagulation and Fibrinolysis, 22 (2011), 756-759.
International Search Report & Written Opinion for PCT/US2010/026377; mailed Oct. 4, 2010; 10 pages.

\* cited by examiner

ENHANCING COAGULATION OR REDUCING FIBRINOLYSIS

CROSS-REFERENCE TO PRIORITY APPLICATIONS

This application claims priority to U.S. Provisional Application No. 61/157,719, filed Mar. 5, 2009, which is incorporated herein by reference in its entirety.

BACKGROUND

Bleeding must be controlled under a variety of circumstances. For example, injury, illness, or surgery can result in bleeding, and clinicians use a variety of measures to control such bleeding in their patients. Such control, however, can be particularly difficult if the patient is on certain medications or has certain conditions, such as hemophilia.

SUMMARY

Compositions and methods for controlling bleeding in a subject are provided herein. Enhancing coagulation and reducing fibrinolysis are used throughout as means for controlling bleeding in a subject. The methods include selecting a subject in need of enhanced coagulation or reduced fibrinolysis, and administering to the subject a carbon monoxide releasing molecule (CORM) or a pharmaceutically acceptable salt thereof. Examples of CORMs and pharmaceutically acceptable salts thereof useful with the methods described herein include tricarbonyldichloro-ruthenium (II) dimer (i.e., CORM-2), tricarbonylchloro(glycinato) ruthenium (II) (i.e., CORM-3), sodium boranocarbonate, dimanganese decacarbonyl, iron pentacarbonyl, and derivatives thereof. Also provided are compositions including a CORM or a pharmaceutically acceptable salt thereof and a blood product. The blood product can be, for example, a cryoprecipitate or fresh frozen plasma. Methods of treating a subject in need of a blood product are provided, which include administering to the subject the composition comprising the CORM or a pharmaceutically acceptable salt thereof and a blood product.

The details of one or more examples of the compositions and methods are set forth in the accompanying drawings and the description below. Other features, objects, and advantages will be apparent from the description and drawings, and from the claims.

DETAILED DESCRIPTION

Figure 1:
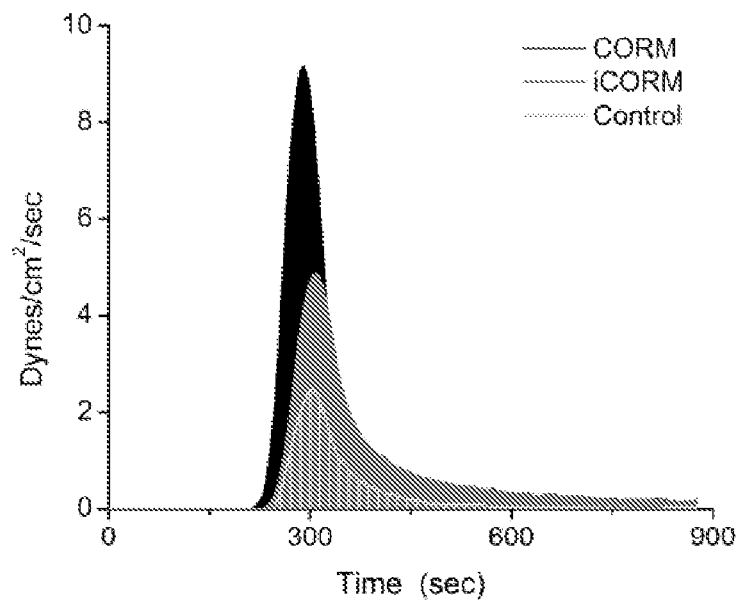
FIG. 1 is a graph showing CORM-2 and inactivated CORM-2 (iCORM-2) enhancement of coagulation kinetics in FXIII deficient plasma. Compared to normal, unexposed plasma (light gray hatch trace), plasma exposed to 100 µM CORM-2 (black trace) or iCORM (gray trace) has significant increases in both the velocity of clot formation and clot strength.

Previous studies have shown that carbon monoxide (CO) generated during degradation of heme by heme oxygenase or pharmacologically administered with carbon monoxide releasing molecules (CORMs) decreases inflammation, promotes vasodilatation, attenuates ischemia-reperfusion injury, and decreases apoptosis. It has also been shown that CO released by CORMs reduces thrombosis in vitro and coagulation in vivo. However, the examples provided herein demonstrate that CO administered with CORMs results in enhanced coagulation and attenuated fibrinolysis, as evidenced by an increased speed of growth and clot strength.

With regard to the antithrombotic effects of CO, a mild decrease in platelet aggregation occurs following exposure to CO gas, which was posited to be secondary to activation of soluble guanylate cyclase (Brune et al., *Mol Pharmacol* 32:497-504 (1987); Brune et al., *Eur J Biochem* 192:683-688 (1990)). It was later determined that 100-500 μM CO released from tricarbonylchloro(glycinato)ruthenium (II) inhibited platelet aggregation in vitro by 25-95% independent of soluble guanylate cyclase activation (Chlopicki et al., *Cardiovasc Res* 71:393-401 (2006)). Further, previous reports showed an anticoagulant effect of CO in vivo (True et al, *Circ Res* 101:893-901 (2007)). The ambient CO concentration in the circulation of the rodent model described in True et al., 2007 was not likely near the 500 μM CO required for marked platelet inhibition in vitro (Chlopicki et al., *Cardiovasc Res* 71:393-401 (2006)), as this would likely be lethal (see Motterlini et al., *Circ Res* 90:e17-e24 (2002) for cytotoxicity in bolus exposure of 170 μM to 420 μM CORM-2 to bovine vascular smooth muscle cells). Thus, the effects of CO on thrombus formulation appear related to the mode of delivery and timing of administration. The examples described herein, in contrast, indicate that exposure of human plasma to tricarbonyldichlororuthenium (II) dimer results in enhanced coagulation and attenuated fibrinolysis, as evidenced by an increased speed of growth and strength of clots.

The compositions and methods described herein are useful in controlling bleeding in a subject. Without meaning to be limiting, the compositions and methods described herein have procoagulant and/or antifibrinolytic effects. The compositions and methods described herein, for example, can be useful in enhancing coagulation or reducing fibrinolysis. The method of enhancing coagulation or reducing fibrinolysis in a subject includes the steps of selecting a subject in need of enhanced coagulation or reduced fibrinolysis and administering to the subject a CORM or a pharmaceutically acceptable salt thereof.

As used herein, a carbon monoxide releasing agent (CORM) refers to a metal carbonyl compound or a pharmaceutically acceptable salt thereof that releases carbon monoxide. The CORM can release carbon monoxide by several methods. For example, the CORM can release carbon monoxide on contact with a suitable solvent or medium, e.g., on contact with an aqueous physiological fluid such as blood or lymph. The CORM can also release carbon monoxide, for example, on contact with physiological cellular materials, such as a tissue, organ, or cell. Another example of a method by which a CORM can release carbon monoxide is by irradiation. The compound may be irradiated prior to administration, for example, to produce a solution of dissolved CO, or may be irradiated in situ after administration.

CORMs and pharmaceutically acceptable salts thereof suitable for the methods described herein include those including a transition metal or metalloid and one or more carbonyl ligand(s). The transition metal or metalloid, for example, can be ruthenium, iron, manganese, cobalt, nickel, molybdenum, rhodium, or boron. The carbonyl ligand(s) can be coordinated to the metal center, or bonded to other groups by ionic or covalent bonds. The CORMs and pharmaceutically acceptable salts thereof for use with the methods described herein can also include additional ligands that may modulate a particular property of the CORM, such as, for example, the rate of releasing carbon monoxide, solubility, hydrophobicity, stability, or electrochemical potential. The additional ligands can be, for example, halides, sulfoxides, natural and synthetic amino acids, aromatics, carboxylates, ethers, alcohols, or nitriles. The CORM or a pharmaceutically acceptable salt thereof may also include a targeting moiety useful for facilitating release of carbon monoxide at an appropriate site. The targeting moiety can be, for example, capable of binding a receptor on a particular target cell surface to promote release of carbon monoxide at the required site.

An example of a CORM or a pharmaceutically acceptable salt thereof suitable for use with the methods described herein is tricarbonyldichlororuthenium (II) dimer (CORM-2). Further examples of CORMs suitable for use with the methods described herein include tricarbonylchloro(glycinato)ruthenium (II) (CORM-3), sodium boranocarbonate, dimanganese decacarbonyl, and iron pentacarbonyl.

The compounds described herein can be prepared in a variety of ways. The compounds can be synthesized using various synthetic methods. At least some of these methods are known in the art of synthetic organic chemistry. The compounds described herein can be prepared from readily available starting materials. Optimum reaction conditions can vary with the particular reactants or solvent used, but such conditions can be determined by one skilled in the art.

Reactions to produce the compounds described herein can be carried out in solvents, which can be selected by one of skill in the art of organic synthesis. Solvents can be substantially nonreactive with the starting materials (reactants), the intermediates, or products under the conditions (e.g., temperature and pressure) at which the reactions are carried out. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatograpy (HPLC) or thin layer chromatography.

The CORMs described herein or pharmaceutically acceptable salts thereof can be provided in a composition including a CORM or a pharmaceutically acceptable salt thereof and a blood product. The blood product can be, for example, a cryoprecipitate or fresh frozen plasma. The CORM for the composition can be selected from any of the CORMs described herein, including, for example, tricarbonyldichlororuthenium (II) dimer, tricarbonylchloro(glycinato)ruthenium (II), sodium boranocarbonate, dimanganese decacarbonyl, iron pentacarbonyl, and derivatives thereof.

One or more of the compounds described herein or pharmaceutically acceptable salts thereof can be provided in a pharmaceutical composition. The pharmaceutical composition can be formulated in accordance with its use and mode of administration. The compositions will include a therapeutically effective amount of one or more of the compounds described herein or derivatives thereof in combination with a pharmaceutically acceptable carrier and, optionally, can further include other agents, including other therapeutic agents. These compositions can be prepared in any manner available in the art and can be administered in a number of ways depending on whether local or systemic treatment is desired, on the area to be treated, the subject to be treated, and other variables. Thus, the disclosed compositions and compounds can be administered, for example, orally, parenterally (e.g., intravenously), intraventricularly, intramuscularly, intraperitoneally, transdermally, extracorporeally, or topically. The compositions and compounds can be administered locally.

By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the compound described herein or pharmaceutically acceptable salts thereof suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like can also be included. Prolonged absorption of the injectable pharmaceutical form can be brought about by the use of agents delaying absorption, for example, aluminum monostearate and gelatin.

Solid dosage forms for oral administration of the compositions described herein or pharmaceutically acceptable salts thereof include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid compositions of a similar type can also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They can contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compositions described herein or pharmaceutically acceptable salts thereof include pharmaceutically acceptable emulsions, solutions, suspensions, syrups, and elixirs. In addition to the active compounds, the liquid dosage forms can contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, can contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or pharmaceutically acceptable salts thereof for rectal administrations are optionally suppositories, which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of the compounds described herein or pharmaceutically acceptable salts thereof include ointments, powders, sprays, and inhalants. For example, the CORMs and pharmaceutically acceptable salts thereof can be formulated as a spray for the nasopharynx, the lung, or skin. The compounds described herein or pharmaceutically salts thereof are admixed under sterile conditions with a physiologically acceptable carrier and any preservatives, buffers, or propellants as can be required. Ophthalmic formulations, ointments, powders, and solutions are also contemplated as being within the scope of the compositions.

The term pharmaceutically acceptable salts as used herein refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These can include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See Stahl and Wermuth, Pharmaceutical Salts: Properties, Selection, and Use, Wiley-VCH, 2008, which is incorporated herein by reference in its entirety, at least, for compositions taught herein.)

The CORMs and pharmaceutically acceptable salts thereof described herein are useful in controlling bleeding in humans (including pediatric and geriatric populations) and animals (e.g., veterinary applications). The methods described herein comprise selecting a subject in need of controlled bleeding and administering to a subject an effective amount of the CORM or a pharmaceutically acceptable salt thereof. Bleeding can be controlled by enhancing coagulation and/or attenuating fibrinolysis.

The methods described herein are useful for subjects that are undergoing surgery, undergoing hemodilution, or have a disease or condition associated with internal or external bleeding. For example, the disease or condition associated with bleeding can be hemophilia, thrombocytopenia, von Willebrand disease, hereditary hemorrhagic telangiectasia, or disseminated intravascular coagulation. Further, the disease or condition associated with bleeding can be an open wound. The open wound can be caused, for example, by trauma, injury, or a surgical procedure. The disease or condition can also be associated with internal bleeding (e.g., a bleeding ulcer or hemoptysis). The CORM or CORM composition can be administered locally or systemically in accordance with the subject's needs. For example, if a subject with hemophilia experiences bleeding into a joint, the CORM or CORM composition can be injected intra-articularly. In the case of a liver laceration or abdominal wound, sterile gauze pads soaked in CORM or CORM compositions can be used to contact the site of bleeding. The methods described herein are also useful for the treatments of subjects with hemophilia and hemophilia-like disorders, including factor VII (FVII), factor VIII (FVIII), and factor IX (FIX) deficiencies as described in Example 4.

The methods described herein are useful for treating a subject in need of a blood product, including subjects that have a disease or condition caused by a bacteria or a virus, subjects who have experienced blood loss, subjects with a chronic disease or condition associated with bleeding (e.g., hemophilia), subjects in need of transfusions (e.g., an Rh-positive infant born to an Rh-negative mother). The method of treating a subject in need of a blood product includes administering to the subject a composition including a CORM or a pharmaceutically acceptable salt thereof and a blood product, as described herein. Examples of infectious diseases or conditions that may be treated with the compositions described herein include subjects with Hepatitis A Virus (HAV) infection, Hepatitis B Virus (HBV) infection, Human Immunodeficiency Virus (HIV) infection, corona virus infection, cytomegalovirus infection (CMV), and severe acute respiratory syndrome (SARS). The compositions described herein may also be useful in the treatment of congenital antithrombin III deficiency, venous and arterial thrombosis, acquired antithrombin III deficiency, disseminated intravascular coagulation, microangiopathic hemolytic anemias, and veno-occlusive disease (VOD).

The methods described herein are useful for subjects in need of increased blood clot formation. These subjects include, for example, those that are concurrently being treated with a therapeutic agent that prevents coagulation, such as anticoagulants (e.g., heparin or warfarin as described in Example 6), antiplatelet medications (e.g., clopidogrel), anti-thrombins (e.g., argatroban, lepirudrin, bivalirudin, or hirudin), or fibrinolytic medications (e.g., urokinase, streptokinase, or tissue type plasminogen activator).

The methods and compounds as described herein are useful for both prophylactic and therapeutic treatment. For prophylactic use, a therapeutically effective amount of the CORMS and pharmaceutically acceptable salts thereof are administered to a subject prior to bleeding or during bleeding. Prophylactic administration can occur for several hours to days prior to the bleeding. Prophylactic administration can be used, for example, in preparation for a surgical procedure. Therapeutic treatment involves administering to a subject an effective amount of the CORMs described herein or pharmaceutically acceptable salts thereof after bleeding has commenced.

Administration of the CORMs described herein or pharmaceutically acceptable salts thereof can be carried out using therapeutically effective amounts of the CORMs described herein or pharmaceutically acceptable salts thereof for periods of time effective to control the bleeding (e.g., the time necessary to enhance coagulation or to reduce fibrinolysis). For example, the CORMs described herein or pharmaceutically acceptable salts thereof can be administered as a single dose (i.e., bolus dosage) or as multiple doses. The effective amount of the CORMs described herein or pharmaceutically acceptable salts thereof can be determined by one of ordinary skill in the art and includes exemplary dosage amounts for a subject of from about 25 $\mu$M to about 200 $\mu$M of the CORM. Alternatively, the dosage amount can be from about 50 $\mu$M to about 100 $\mu$M of the CORM, or about 100 $\mu$M of CORM. Those of skill in the art will understand that the specific dose level and frequency of dosage for any particular subject will vary and will depend upon a variety of factors, including the metabolic stability and length of action of the CORM, the species, the mode and time of administration, the rate of excretion, drug combination, and the type and severity of the particular condition.

The administration of the CORMs described herein or pharmaceutically acceptable salts thereof can be administered systemically or regionally to areas of bleeding to allow carbon monoxide to be available for a controllable time frame (e.g., a half-life of approximately 1 minute). Thus, symptoms that are common after the administration of other hemostatic agents, including persistant activation of coagulation and/or residual hypercoagulability, do not occur.

The method of controlling bleeding in a subject can further comprise administering to the subject an additional agent. Thus, the provided compositions and methods can include one or more additional agents. The one or more additional agents and the CORMs described herein or pharmaceutically acceptable salts thereof can be co-administered. Co-administration, as used herein, includes administration in any order, including simultaneous administration, as well as temporally spaced order of up to several days apart. The methods can also include more than a single administration of the one or more additional agents and/or the CORMs described herein or pharmaceutically acceptable salts thereof. The administration of the one or more additional agents and the CORMs described herein or pharmaceutically acceptable salts can be by the same or different routes and concurrently or sequentially.

The additional agents can include, for example, therapeutic agents. Therapeutic agents include but are not limited to antibiotics, anesthetics, analgesics, antihistamines, antimicrobials, antifungals, antivirals, steroidal and non-steroidal anti-inflammatory agents, chemotherapeutic agents, antibodies, conventional immunotherapeutic agents, cytokines, chemokines, and/or growth factors.

Further, the CORMs described herein or pharmaceutically acceptable salts thereof can be co-administered with additional agents that aid in controlling bleeding. For example, the CORMs described herein or pharmaceutically acceptable salts thereof can be co-administered with a hemostatic agent, a coagulant, or an anti-fibrinolytic medication. Examples of anti-fibrinolytic agents useful with the methods described herein include aminocaproic acid and tranexamic acid. Other agents that are useful in controlling bleeding, including blood coagulation factors (e.g., factor VIII, factor IX, factor XIII, von Willebrand's factor), fibrin, thrombin, recombinant activated factor VII, prothrombin complex concentrate, and FEIBA (Baxter, Vienna, Austria), can also be co-administered with the CORMs described herein or pharmaceutically acceptable salts thereof.

Any of the aforementioned therapeutic agents can be used in any combination with the compositions described herein. Combinations are administered either concomitantly (e.g., as an admixture), separately but simultaneously (e.g., via separate intravenous lines into the same subject), or sequentially (e.g., one of the compounds or agents is given first followed by the second). Thus, the term combination is used to refer to either concomitant, simultaneous, or sequential administration of two or more agents.

The CORMs described herein or pharmaceutically acceptable salts thereof, with or without additional agents, can be administered at or near the site of bleeding. The CORMs can also be administered, for example, topically, locally, intravenously, or intramuscularly. Further, the CORM can be formulated for administration, for example, by aerosol sprays, ointments, sutures, bandages, surgical dressings, wound packings, gauze, swabs, liquids, pastes, creams, lotions, foams, gels, emulsions, or powders. The CORMs can also be used to coat needles or minimally invasive probes (e.g., an endoscope). Dental instruments, dental floss, and mouth wash preparations are also useful formulations for administering CORMs, where bleeding gums or the like can be problematic. Thus, provided herein are aerosol sprays, ointments, sutures, bandages, surgical dressings, wound packings, gauze, swabs, liquids, pastes, creams, lotions, foams, gels, emulsions, powders, needles, probes, dental instruments, dental floss, and mouth wash comprising a CORM.

CORMs that have released all of the carbonyl ligands as carbon monoxide (i.e., inactive CORM or iCORM) are also useful with the methods described herein. These molecules are able to enhance the velocity of clot formation and clot strength, as shown in Example 2.

As used throughout, subject can be a vertebrate, more specifically a mammal (e.g. a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with a disease or disorder. The term patient or subject includes human and veterinary subjects.

As used herein the terms treatment, treat, or treating refers to a method of reducing the effects of a disease or condition or symptom of the disease or condition or a delay in the onset of additional signs or symptoms of the disease or condition. Thus in the disclosed method, treatment can refer to a 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is a 10% reduction in one or more symptoms or signs of the disease in a subject as compared to a control. Thus the reduction can be a 10%, 20%, 30%, 40%, 50%, 60%, 70%, 80%, 90%, 100%, or any percent reduction between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refers to an action, for example, administration of a composition or therapeutic agent, that occurs before or at about the same time a subject begins to show one or more symptoms of the disease or disorder, which inhibits or delays onset or severity of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

As used herein the terms reduce and reducing refer to attenuating the effects of a disease or condition (e.g., hemophilia) or symptom of the disease or condition by decreasing a parameter as compared to the level of the parameter in a control. Thus, in the disclosed method, reducing can refer to a 10%, 20%, 30%, 40%, 50%, 60%, 70%, 80%, 90%, or 100% decrease in the severity of an established disease or condition (e.g., a decrease in the number of hospitalizations) or symptom (e.g., a decrease in clotting time). For example, a method for reducing a disease is considered to be effective if there is a 10% decrease in one or more symptoms or signs (e.g., rate of bleeding) of the disease in a subject as compared to a control. Thus the reduction can be a 10%, 20%, 30%, 40%, 50%, 60%, 70%, 80%, 90%, 100%, or any percent decrease in between 10% and 100% as compared to native or control levels. It is understood that reducing does not necessarily refer to a cure or complete ablation of the disease, condition, or symptom(s) of the disease or condition.

As used herein the terms enhance and enhancing refer to attenuating the effects of a condition or process by promoting or increasing a parameter as compared to the parameter in a control. Thus, in the disclosed method, enhancing can refer to a 10%, 20%, 30%, 40%, 50%, 60%, 70%, 80%, 90%, or 100% increase in the desired outcome of a condition or process. For example, a method for enhancing coagulation is considered to be effective if there is a 10% increase in one or more symptoms or signs (e.g., strength of a blood clot) of the condition or process in a subject as compared to a control. Thus the enhancement can be a 10%, 20%, 30%, 40%, 50%, 60%, 70%, 80%, 90%, 100%, or any percent increase in between 10% and 100% as compared to native or control levels.

By control is meant the same subject before or after any CORM effect or a different untreated subject or known average for untreated subjects.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Throughout this application, various publications are referenced. The disclosures of these publications in their entireties are hereby incorporated by reference into this application.

A number of aspects have been described. Nevertheless, it will be understood that various modifications may be made. Furthermore, when one characteristic or step is described it can be combined with any other characteristic or step herein even if the combination is not explicitly stated. Accordingly, other aspects are within the scope of the claims.

The examples below are intended to further illustrate certain aspects of the methods and compounds described herein, and are not intended to limit the scope of the claims.

EXAMPLES

Example 1

Effects of Carbon Monoxide Releasing Agents on Coagulation

Materials and Methods

Pooled normal plasma (George King Bio-Medical, Overland Park, Kans.) anticoagulated with sodium citrate was utilized for experimentation. This lot of plasma had a prothrombin time of 12.7 seconds, an activated partial thromboplastin time of 29.6 seconds, and a fibrinogen concentration greater than 250 mg/dL. Factor XIII (FXIII) deficient plasma anticoagulated with sodium citrate was also obtained from George King Bio-Medical (Overland Park, Kans.).

Plasma Sample Composition. The final volume for all subsequently described plasma sample mixtures was 359.4 µL. The sample composition consisted of 316 µL of plasma; 10 µL of tissue factor (0.1% final concentration in 0.9% NaCl; Diagnostica Stago, Asnieres, France) or 1% celite in 0.9% NaCl (0.28 mg/mL final concentration), 3.6 µL of dimethyl sulfoxide (DMSO) or DMSO with tricarbonyldichlororuthenium (II) dimer (CORM-2, 100 µM final concentration; Sigma-Aldrich, St. Louis, Mo.) or DMSO with inactivated CORM-2 (iCORM-2, 100 µM final concentration), 10 µL of $dH_2O$, and 20 µL of 200 mM calcium chloride ($CaCl_2$). CORM-2 was rendered inactive by being placed in DMSO for three days until the solution changed from a yellow to clear solution, indicative of completion of CO release. This concentration of CORM-2 was chosen because the concentration of CO released would be expected to be in the mid to lower ranges used in previously reported ex vivo, in vitro, and cell-based experiments (Motterlini et al., *Circ Res* 90:e17-e24 (2002); Megias et al., *Br J Pharm* 150:977-986 (2007); Chlopicki et al., *Cardiovasc Res* 71:393-401 (2006); Dong et al., *Eur J Pharmacol* 590:99-104 (2008), which are incorporated by reference herein in their entireties). Also, 0.75 mol of CO is released from every mole of CORM-2, with a CO release half-life of 1 minute once placed in aqueous solution (pH=7.4) at a temperature of 37° C. (Motterlini et al., *Expert Opin Investig Drugs,* 14:1305-1318 (2005), which is incorporated by reference herein in its entirety). While CORM-2 decays slowly in DMSO, DMSO was added to the dry compound just prior to placement in the plasma mixure.

Clot Lifespan Model Analyses. Plasma sample mixtures were placed in a disposable cup in a computer-controlled THROMBELASTOGRAPH® hemostasis system (Model 5000, Haemoscope Corp., Niles, Ill.), with addition of $CaCl_2$ as the last step to initiate clotting. Data were collected for 15 minutes, as normal plasma completes thrombus formation within this interval in this system (Dong et al., *Eur J Pharmacol* 590:99-104 (2008)). The following previously described variables (Nielsen et al., *Acta Anaesthesiol Scand* 49:222-231 (2005) and Nielsen et al., *Blood Coagul Fibrinolysis* 17:75-81 (2006), which are incorporated by reference herein in their entireties) were determined at 37° C.: Time to maximum rate of thrombus generation (TMRTG, the time interval (sec) observed prior to maximum speed of clot growth); Maximum rate of thrombus generation (MRTG, the maximum velocity of clot growth observed (dynes/$cm^2$/sec); Total Thrombus Generation (TTG, the total area under the velocity curve during clot growth (dynes/$cm^2$), representing the amount of clot strength generated during clot growth).

Statistical Analyses. Data are presented as mean±SD. All conditions described were represented with n=8 experiments, as n=6-8 typically provides statistical power>0.8 in similar analyses (Nielsen et al., *Acta Anaesthesiol Scand* 49:222-231 (2005) and Nielsen et al., *Blood Coagul Fibrinolysis* 17:75-81 (2006)). Analyses of the effects of CORM-2 and iCORM-2 on thrombelastographic variables were conducted using one way analysis of variance with the Holm-Sidak test used for post hoc comparisons. Graphical representation of the data was generated with commercially available software (Origin 7.5, OriginLab Corp., Northampton, Mass.). A P value of ≤0.05 was considered significant.

Results

Following tissue factor activation, both CORM-2 and iCORM-2 exposure enhanced coagulation, demonstrated by a significant decrease in the time to onset of coagulation, increase in the velocity of clot growth, and increase in clot strength (Table 1). Notably, plasma exposed to CORM-2 had a velocity of clot growth by more than double of unexposed samples, whereas samples exposed to CORM-2 had a velocity of clot growth more than double that of unexposed samples, whereas samples exposed to iCORM had only a 50% increase. With regard to clot strength, this hierarchical pattern of CORM-2 exposed>iCORM-2 exposed>unexposed plasma was also observed. Following Celite activation, as displayed in Table 1, there was no effect on the time of onset of coagulation, but the same hierarchical pattern of CORM-2 exposed>iCORM-2 exposed>unexposed plasma was observed when the velocity of clot formation and clot strength were considered.

In order to determine if this apparent common pathway-dependent enhancement of coagulation was FXIII-dependent, FXIII deficient plasma was activated with Celite and exposed to CORM-2 and iCORM-2 in a third series of experiments. As seen in Table 1 and FIG. 1, the velocity of clot growth and clot strength were significantly increased with the same pattern observed in normal plasma (CORM-2>iCORM-2>DMSO vehicle).

TABLE 1

Thrombelastographic Coagulation Values in Normal and FXIII Deficient Plasma

|  | 0 μM CORM-2 | 100 μM iCORM-2 | 100 μM CORM-2 |
|---|---|---|---|
| TF-Activated Normal Plasma | | | |
| TMRTG (sec) | 188 ± 17 | 169 ± 12* | 156 ± 13* |
| MRTG (dynes/cm$^2$/sec) | 4.1 ± 0.6 | 5.9 ± 0.5* | 9.1 ± 0.9*† |
| TTG (dynes/cm$^2$) | 164 ± 15 | 221 ± 20* | 273 ± 21*† |
| Celite-Activated Normal Plasma | | | |
| TMRTG (sec) | 202 ± 8 | 199 ± 4 | 188 ± 18 |
| MRTG (dynes/cm$^2$/sec) | 8.8 ± 0.6 | 11.2 ± 0.5* | 13.7 ± 1.3*† |
| TTG (dynes/cm$^2$) | 158 ± 1.1 | 206 ± 10* | 248 ± 17*† |
| Celite-Activated FXIII Deficient Plasma | | | |
| TMRTG (sec) | 290 ± 18 | 282 ± 14 | 296 ± 13 |
| MRTG (dynes/cm$^2$/sec) | 2.5 ± 0.3 | 5.0 ± 0.5* | 9.1 ± 1.2*† |
| TTG (dynes/cm$^2$) | 48 ± 7 | 117 ± 11* | 163 ± 21*† |

*$P < 0.05$ vs. 0 μM CORM-2;
†$P < 0.05$ vs. 100 μM iCORM-2

Discussion

Both CO and the inactivated carrier molecule derived from CORM-2 enhance coagulation in plasma. Without meaning to be limited by theory, enhancement of thrombin-fibrinogen interactions (and perhaps enhancement of fibrinogen) appears to be the primary mechanism responsible for CORM-2 mediated increases in coagulation kinetics, based on the data obtained with FXIII-deficient plasma. In fact, the addition of CORM-2 to FXIII-deficient plasma was equivalent to 100% replacement of FXIII activity with regard to enhancement of coagulation kinetics. Therefore, under conditions of CO exposure commonly utilized in a variety of experimental settings, CORM-2 exposure results in markedly enhanced velocity of thrombus formation and strength.

The thrombelastographic data show that progressively increased thrombin generation with progressively greater tissue factor activity shortened the onset of coagulation without increasing either the velocity of clot growth or clot strength in normal plasma. In fact, clot strength decreased with progressive increases of thrombin generation in this model. The data described herein demonstrated that CORM-2 mediated decreases in the time to maximum rate of thrombus generation only occurred in tissue factor activated samples, and the degree of decrease is minimal compared to the changes in the velocity of clot formation and clot strength. Also, the 1 minute half-life of CO liberation from CORM-2 likely resulted in essentially all of the 75 μM of CO that is releasable by 100 μM CORM-2 to be present when the maximum rate of thrombus generation is observed. Thus, given the either absent or minimal decrease in time to onset of coagulation coupled with the remarkable enhancement of the velocity of clot growth and strength, CORM-2 increased the ability of fibrinogen to be polymerized by thrombin in a manner similar to an FXIII-like molecule.

Example 2

Effects of Carbon Monoxide Releasing Agents on Fibrinolysis

Materials and Methods

Pooled normal plasma (George King Bio-Medical, Overland Park, Kans.) anticoagulated with sodium citrate was utilized for experimentation. The lot of plasma had a prothrombin time (PT) of 12.7 seconds, an activated partial thromboplastin time (aPTT) of 29.6 seconds, and a fibrinogen concentration greater than 250 mg/dl. Factor XIII (FXIII) deficient plasma anticoagulated with sodium citrate was also obtained from the same vendor. The following immunodepleted plasma types were obtained from Affinity Biologicals, Inc, (Ancaster, Ontario, Canada): plasminogen activator inhibitor type 1 (PAI-1) deficient plasma (<0.5 ng/mL) with a PT of 14.3 seconds, an aPTT of 38.5 seconds, and a fibrinogen concentration of 353 mg/dl; thrombin activatable fibrinolysis inhibitor (TAFI) deficient plasma (<0.01 U/mL) with a PT of 10.5 seconds, an aPTT of 36.2 seconds, and a fibrinogen concentration of 234 mg/dL; and, $\alpha_2$-antiplasmin deficient plasma (<0.01 U/ml) with a PT of 10.0 seconds, an aPTT of 35.3 seconds, and a fibrinogen concentration of 332 mg/dL.

Plasma Sample Composition. The final volume for all subsequently described plasma sample mixtures was 359.4 μL. Sample composition consisted of 316 μL of plasma; 10 μL of tissue factor (0.1% final concentration in 0.9% NaCl; Diagnostica Stago, Asnieres, France), 3.6 μL of dimethyl sulfoxide (DMSO) or DMSO with CORM-2 (Sigma-Aldrich, St. Louis, Mo.) or DMSO with inactivated CORM-2 (iCORM-2), 10 μL of tissue-type plasminogen activator (tPA, 580 U/μg, Genentech, Inc., San Francisco, Calif.) diluted with 10 mM potassium phosphate buffer (pH 7.4) for a final activity of 100 IU/mL, and 20 μL of 200 mM $CaCl_2$. CORM-2 was rendered inactive by being placed in DMSO for three days until the solution changed from a yellow to clear solution, indicative of completion of CO release. This concentration of CORM-2 was chosen because the concentration of CO released would be expected to be in the mid to lower ranges used in previously reported ex vivo, in vitro, and cell-based experiments (Motterlini et al. 2002; Megias et al. 2007; Chlopicki et al. 2006; Dong et al. 2008). Also, 0.75 mol of CO is released from every mole of CORM-2, with a CO release half-life of 1 min once placed in aqueous solution pH=7.4 at a temperature of 37° C. (Motterlini et al. 2005). While CORM-2 decays slowly in DMSO, DMSO was added to the dry compound just prior to placement into the plasma mixture. The specific series of experiments are subsequently presented.

Concentration-Response Relationships of CORM-2 and iCORM-2 with Clot Lifespan Model (CLSM) Parameters. Normal plasma was exposed to 0, 25, 50, 100 or 200 μM CORM-2 (n=4 per concentration. Additional plasma samples were exposed to 25, 50 or 100 μM iCORM-2 (n=4 per concentration). Samples underwent CLSM analyses as subsequently described.

Comparison of the Effects of CORM-2 and iCORM-2 on CLSM Parameters in Normal Plasma. Given the results of the aforementioned experiments, additional samples of normal plasma were exposed to 0 or 100 μM of CORM-2 or iCORM-2 (n=4 per additional sample condition, n=8 per condition for final analyses). Samples underwent CLSM analyses as subsequently described.

Assessment of the Effects of CORM-2 on CLSM Parameters in FXIII, PAI-1, TAFI and $\alpha_2$-antiplasmin Deficient Plasmas. These experiments were performed to elucidate the roles played by antifibrinolytic enzymes during CORM-2 mediated modulation of fibrinolysis. Samples of the various deficient plasmas were exposed to 0 or 100 µM of CORM-2 (n=8 per condition). Samples underwent CLSM analyses as subsequently described.

Figure 2:
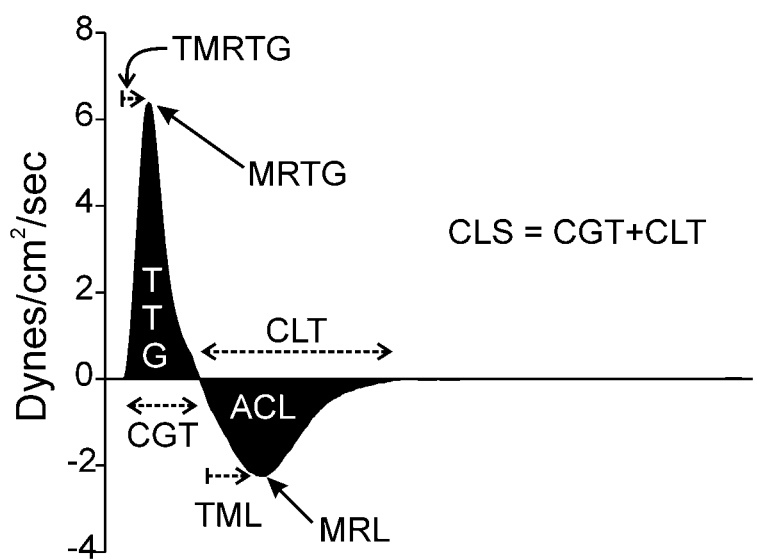
FIG. 2 is a graph illustrating the clot lifespan model variable definitions. CGT=clot growth time (sec), defined as the time when clot formation commences (clot strength of 102 dynes/cm$^2$ [2 mm amplitude]) to when maximum clot strength is observed; CLT=clot lysis time (sec) begins when maximum clot strength is observed and continues until lysis renders clot strength equal to 102 dynes/cm$^2$; CLS=clot lifespan (sec) is the sum of CGT and CLT; TMRTG=time to maximum rate of thrombus generation (sec); MRTG=maximum rate of thrombus generation (dynes/cm$^2$/sec); TTG=total thrombus generation (dynes/cm$^2$); TML=time to maximum rate of lysis (sec); MRL=maximum rate of lysis (-dynes/cm$^2$/sec); ACL=area under the curve of lysis (-dynes/cm$^2$).

Clot Lifespan Model Analyses. As described in Example 1, plasma sample mixtures were placed in a disposable cup in a computer-controlled THROMBELASTOGRAPH® hemostasis system (Model 5000, Haemoscope Corp., Niles, Ill.), with addition of $CaCl_2$ as the last step to initiate clotting. Data were collected until clot lysis time occurred. The following variables were determined at 37° C.: clot growth time (CGT, time from clot amplitude of 2 mm [102 dynes/cm$^2$] until maximum strength is achieved, in sec); clot lysis time (CLT, time from when maximum strength was observed to 2 mm amplitude, in sec); and clot lifespan (CLS, the sum of CGT and CLT). Additional elastic modulus-based parameters previously described were determined (Nielsen et al. 2006) and are displayed in FIG. 2. In addition to the nomenclature described in Example 1, the following terms are defined as follows: Time to maximum rate of lysis (TMRL, the time interval (sec) measured from the time of maximum strength to the time when the velocity of clot disintegration is maximal); Maximum Rate of Lysis (MRL, the maximum velocity of clot disintegration observed (-dynes/cm$^2$/sec)); Area of Clot Lysis (ACL, the total area under the velocity curve during clot disintegration (-dynes/cm$^2$), representing the amount of clot strength lost during clot disintegration). As this model involves complete fibrinolysis, TTG is equivalent to ACL, so ACL was not presented as it provides no additional information.

Statistical Analyses. Data are presented as median (1$^{st}$, 3$^{rd}$ quartiles). All conditions described were represented with n=8 experiments, as n=6-8 typically provides statistical power >0.8 in similar analyses (Example 1; Nielsen et al. 2005; Nielsen et al. 2006; Nielsen et al. 2004). Nonlinear and linear analyses and curve fitting of the various CORM-2 concentrations effects on CLSM variables were performed with commercially available software (SigmaPlot 11.0, Systat Software, Inc., San Jose, Calif.). Analyses of the effects of CORM-2 and iCORM-2 on CLSM variables in normal plasma were conducted with Kruskal-Wallis one way analysis of variance on ranks, whereas Mann-Whitney rank sum tests were used to assess the effects of CORM-2 on CLSM variables in the various immunodepleted/congenitally deficient plasma types (SigmaStat 3.1, Systat Software, Inc., San Jose, Calif.). Graphical representation of the data was generated with commercially available software (SigmaPlot 11.0, Systat Software, Inc., San Jose, Calif.; CorelDRAW 12.0, Corel Corporation, Ottawa, Ontario, Canada; Origin 7.5, OriginLab Corp., Northampton, Mass.). A P value of <0.05 was considered significant.

Results

Figure 3:
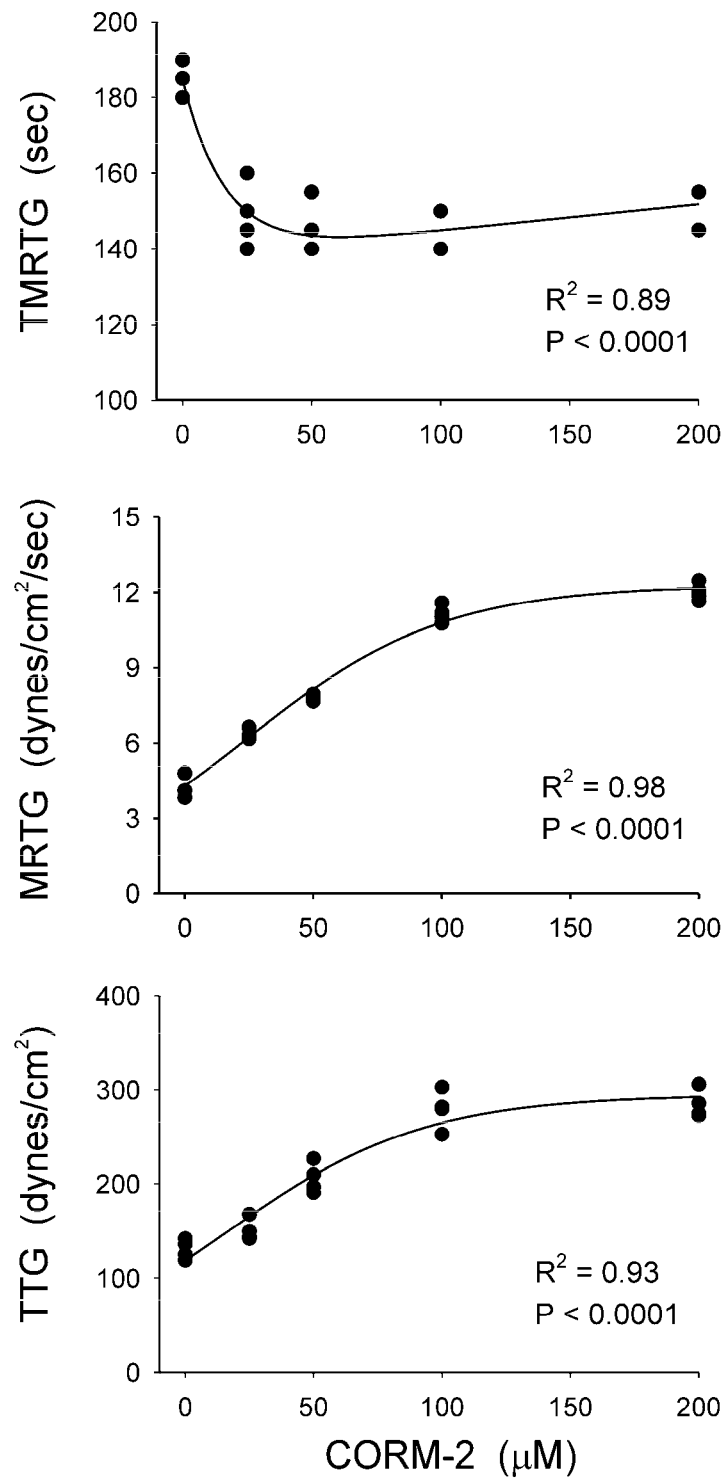
FIG. 3 shows concentration-response relationships of clot growth kinetics and strength with increasing CORM-2 concentration. CORM-2 decreased the time to maximum rate of thrombus generation (TMRTG) (top panel), increased the maximum rate of thrombus generation (MRTG) (middle panel), and increased total thrombus generation (TTG) (bottom panel) in a concentration-dependent manner.
Figure 4:
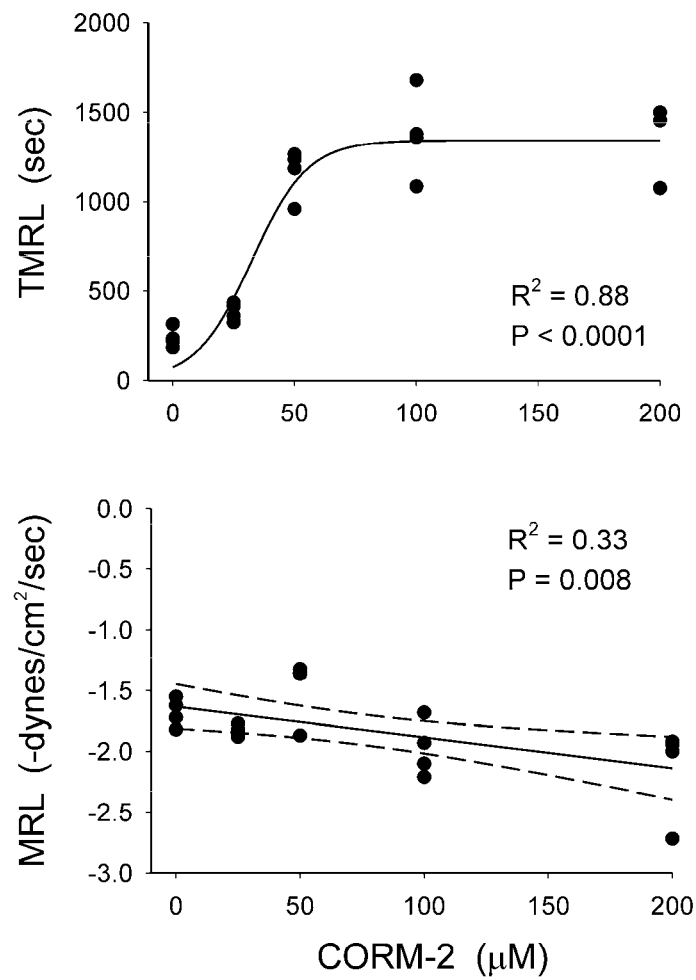
FIG. 4 shows concentration-response relationships of clot fibrinolytic kinetics with increasing CORM-2 concentration. CORM-2 prolonged the time to maximum rate of lysis (TMRL) (top panel) and increased the maximum rate of lysis (MRL) (bottom panel) in a concentration-dependent fashion.
Figure 5:
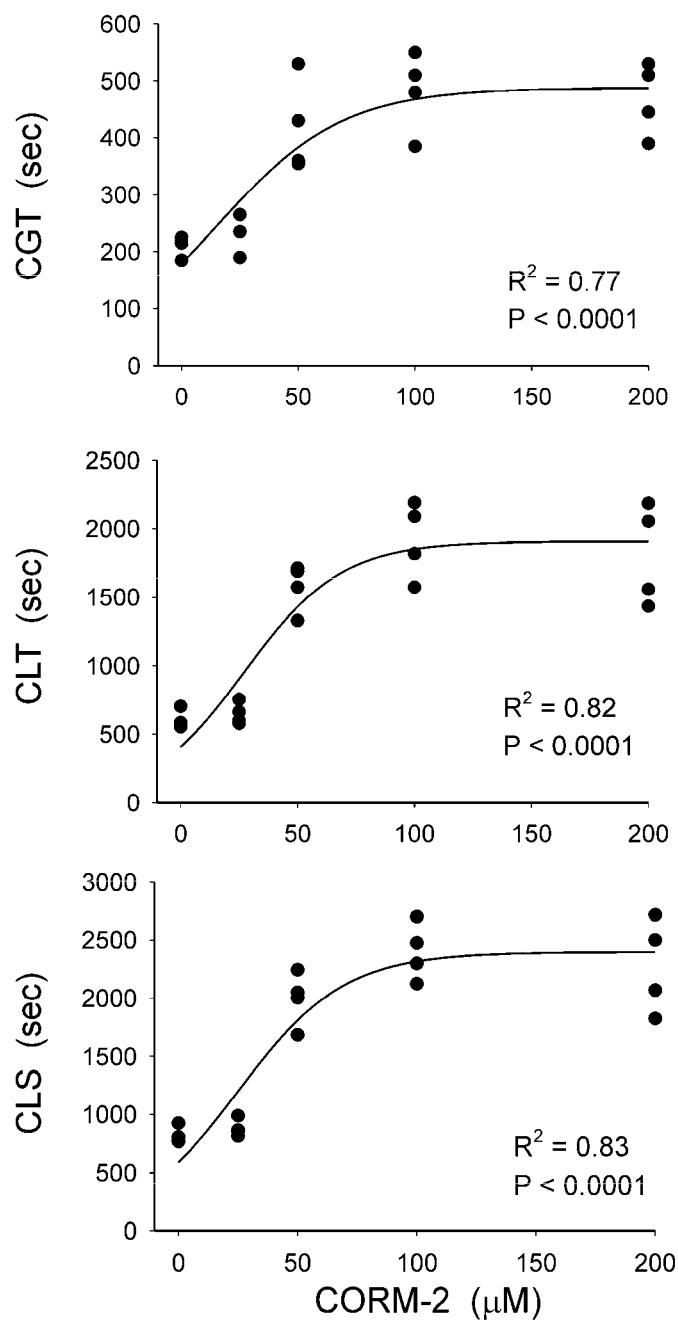
FIG. 5 shows concentration-response relationships of clot growth time (top panel), clot lysis time (middle panel), and clot lifespan (bottom panel) with increasing CORM-2 concentration. CORM-2 increased clot growth time (CGT), clot lysis time (CLT) and clot lifespan (CLS) in a concentration-dependent manner.

Concentration-Response Relationships of CORM-2 and iCORM-2 with CLSM Parameters. As displayed in FIGS. 3-5, CORM-2 enhanced the onset and velocity of thrombus formation in a concentration-dependent fashion. Further, clot strength was also increased by CORM-2 in a concentration-dependent manner. With regard to fibrinolysis, CORM-2 markedly attenuated the onset of fibrinolysis and mildly increased the speed of fibrinolysis. The summation of these effects was enhancement of CGT, CLT and CLS as seen in FIG. 5. The CLSM parameter-specific curves describing the relationship between CORM-2 concentration and thrombus growth/disintegration kinetics are displayed in Table 2.

iCORM exposure resulted in marked, concentration-dependent enhancement of fibrinolysis. Results of the experiments with 100 µM iCORM samples are presented in Table 3.

Figure 6:
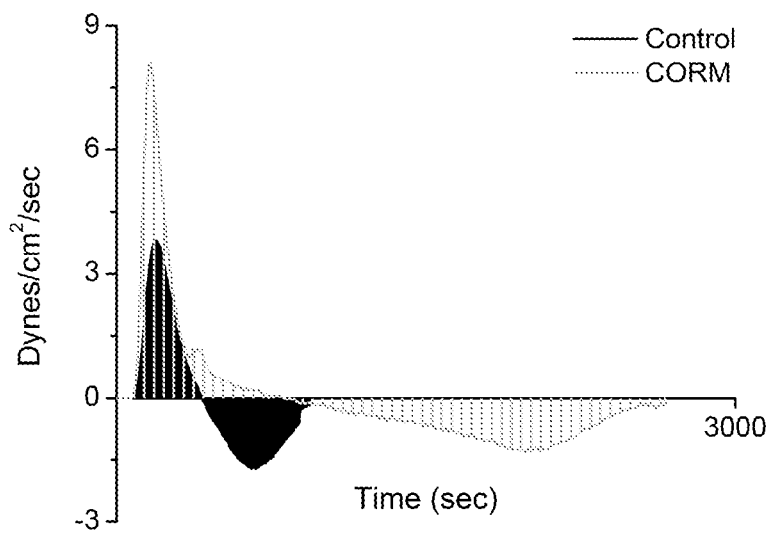
FIG. 6 is a graph showing the effect of CORM-2 on clot growth/disintegration in normal plasma. Exposure of normal plasma to 100 µM CORM-2 (gray trace) resulted in significantly stronger, longer-lasting thrombi compared to unexposed plasma (black trace).
Figure 7:
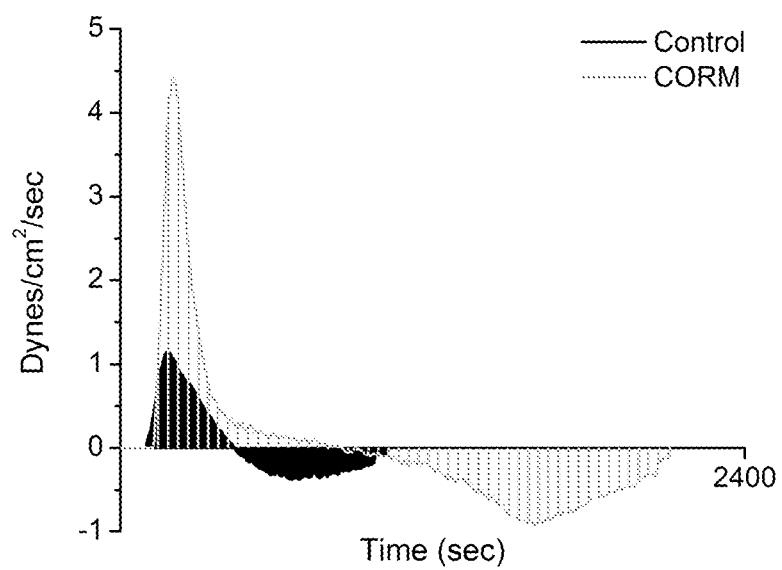
FIG. 7 is a graph showing the effect of CORM-2 on clot growth/disintegration in FXIII deficient plasma. As with normal plasma, exposure of FXIII deficient plasma to 100 µM CORM-2 (gray trace) resulted in significantly stronger, longer-lasting thrombi compared to unexposed plasma (black trace).
Figure 8:
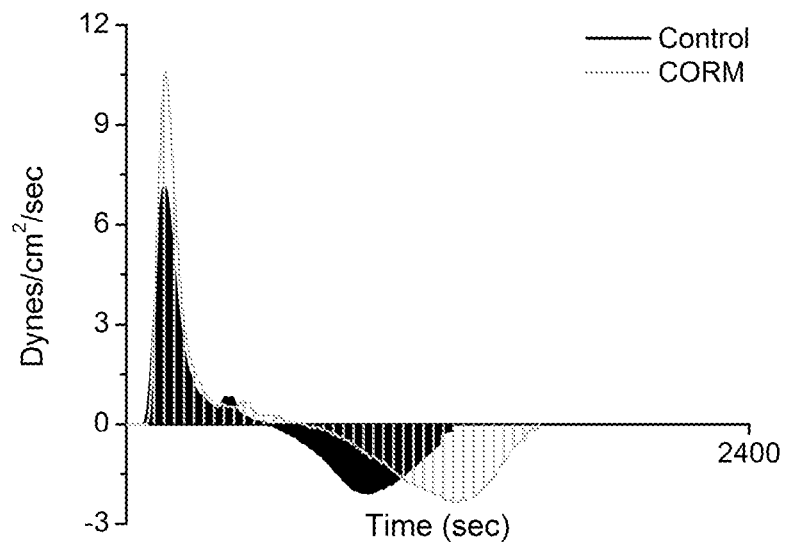
FIG. 8 is a graph showing the effect of CORM-2 on clot growth/disintegration in PAI-1 deficient plasma. Exposure of PAI-1 deficient plasma to 100 µM CORM-2 (gray trace) resulted in significantly stronger, longer-lasting thrombi compared to unexposed plasma (black trace). However, the degree of enhancement of coagulation and attenuation of fibrinolysis by CORM-2 was less than that observed in normal plasma.
Figure 9:
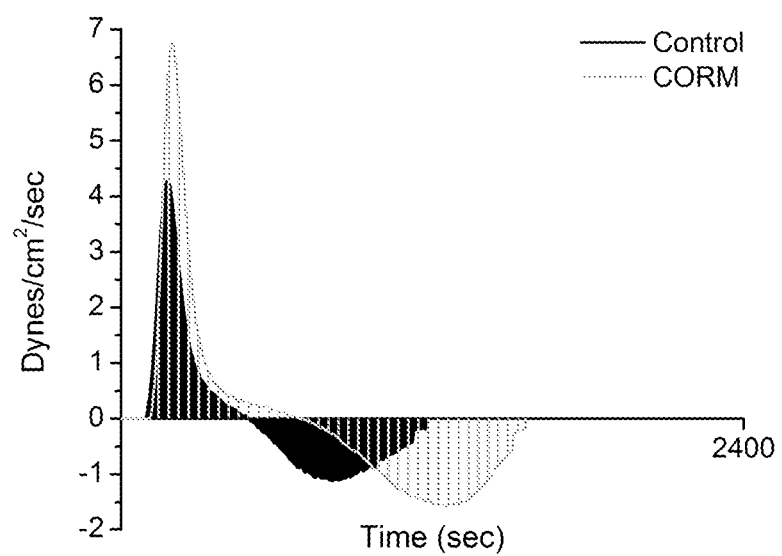
FIG. 9 is a graph showing the effect of CORM-2 on clot growth/disintegration in TAFI deficient plasma. Exposure of TAFI deficient plasma to 100 µM CORM-2 (gray trace) resulted in significantly stronger, longer-lasting thrombi compared to unexposed plasma (black trace). However, the degree of enhancement of coagulation and attenuation of fibrinolysis by CORM-2 was less than that observed in normal plasma, but similar to that observed in PAI-1 deficient plasma.
Figure 10:
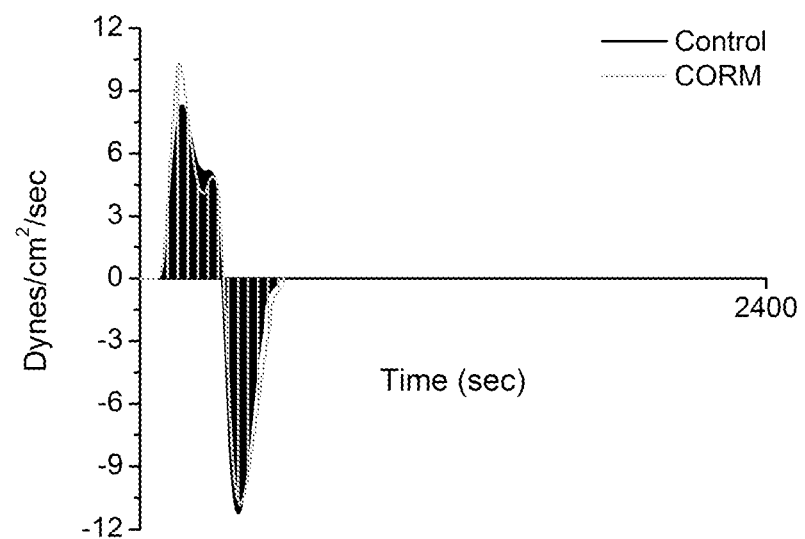
FIG. 10 is a graph showing the effect of CORM-2 on clot growth/disintegration in $\alpha_2$-antiplasmin deficient plasma. Exposure of $\alpha_2$-antiplasmin deficient plasma to 100 µM CORM-2 (gray trace) resulted in very little change in either coagulation or fibrinolytic kinetics compared to unexposed plasma (black trace). This result was markedly different from all other plasma types tested.

Comparison of the Effects of CORM-2 and iCORM-2 on CLSM Parameters in Normal Plasma. As displayed in FIG. 6 and Table 3, 100 µM CORM-2 significantly decreased the time to the onset of coagulation, enhanced the velocity of growth (120%) and strength of the clot (113%), and delayed the onset of fibrinolysis (258%) compared to samples not exposed to CORM-2. The summation of these CORM-2 mediated events kinetic events was a significant increase in CGT (126%), CLT (143%) and CLS (145%) compared to plasma exposed to 0 µM CORM-2. In sharp contrast, while exposure to 100 µM iCORM-2 significantly increased the velocity of thrombus formation and clot strength compared to unexposed samples, this enhancement of coagulation kinetics was markedly less than that observed with CORM-2. Further, iCORM-2 exposure significantly decreased the onset of fibrinolysis (by 46%) and increased the velocity of fibrinolysis (by 107%), with the sum effect being a marked decrease in CLT and CLS. Given these results, only CORM-2 was utilized in the subsequently described experiments to assess the effects of CO on fibrinolysis in the absence of key antifibrinolytic proteins.

Assessment of the Effects of CORM-2 on CLSM Parameters in FXIII, PAI-1, TAFI and $\alpha_2$-antiplasmin Deficient Plasmas. The effects of CORM-2 on thrombus formation/disintegration in the various deficient plasmas are depicted in FIGS. 7-10 and Tables 4-5. In FXIII deficient plasma (Table 4, FIG. 7), as in normal plasma, CORM-2 exposure significantly enhanced the speed of clot formation, clot strength, and prolonged the onset of fibrinolysis compared to unexposed plasma. Despite an increase in MRL, samples exposed to CORM-2 had a significantly greater CLT. Taken as a whole, the magnitude of CORM-2 mediated enhancement of coagulation and attenuation of fibrinolysis in FXIII deficient plasma was similar to that observed in normal plasma.

In PAI-1 deficient plasma (Table 4, FIG. 8), the effects of CORM-2 exposure on the velocity of clot growth and clot strength were significant, but not as marked as that observed in normal plasma. Similarly, while the onset of fibrinolysis was significantly increased by CORM-2 with a concomitant prolongation of CLT in PAI-1 deficient plasma, these changes were not as remarkable as that observed in normal plasma exposed to CORM-2.

In TAFI deficient plasma (Table 5, FIG. 9), CORM-2 exposure significantly increased the velocity of growth and strength of thrombi, but to a far lesser extent than that observed in normal plasma. Similarly, the onsets of fibrinolysis and CLT were significantly prolonged in TAFI deficient plasma by CORM-2, but to a smaller degree than that seen in normal plasma. In sum, PAI-1 and TAFI appeared to have similar importance to CORM-2 mediated attenuation of fibrinolysis.

Last, in $\alpha_2$-antiplasmin deficient plasma (Table 5, FIG. 10), CORM-2 exposure had very limited effects. With regard to clot growth, only the velocity of clot formation was significantly increased by 35%. As for fibrinolysis, CORM-2 exposure significantly prolonged CLT by only 23%, without any significant change in TMRL. Overall, CLS was significantly increased by only 14% following CORM-2 exposure in $\alpha_2$-antiplasmin deficient plasma. Taken as a whole, when these data were compared to all other plasma types, CORM-2 mediated effects on clot formation/disintegration kinetics were more dependent on $\alpha_2$-antiplasmin activity than on any other antifibrinolytic protein tested.

TABLE 2

Curve Fitting Equations Describing the Relationship of CLSM Parameters with CORM-2 Concentrations.

| Parameter | Equation Category | Equation |
|---|---|---|
| TMRTG | Modified Exponential | TMRTG = 138 + 47.2$^{(-0.06[CORM-2])}$ + 0.07[CORM-2] |
| MRTG | Sigmoidal | MRTG = 295/(1 + e$^{-(([CORM-2]-24.0)/38.5)}$) |
| TTG | Sigmoidal | TTG = 295/(1 + e$^{-(([CORM-2]-15.6)/38.8)}$) |
| TMRL | Sigmoidal | TMRL = 1343/(1 + e$^{-(([CORM-2]-32.5)/11.4)}$) |
| MRL | Linear Regression | MRL = −1.63 − (0.002[CORM-2]) |
| CGT | Sigmoidal | CGT = 488/(1 + e$^{-(([CORM-2]-14.8)/27.1)}$) |
| CLT | Sigmoidal | CLT = 1908/(1 + e$^{-(([CORM-2]-27.2)/20.8)}$) |
| CLS | Sigmoidal | CLS = 2397/(1 + e$^{-(([CORM-2]-25.0)/22.3)}$) |

TMRTG = time to maximum rate of thrombus generation (sec); MRTG = maximum rate of thrombus generation (dynes/cm$^2$/sec); TTG = total thrombus generation (dynes/cm$^2$); TMRL = time to maximum rate of lysis (sec); MRL = maximum rate of lysis (−dynes/cm$^2$/sec); CGT = clot growth time (sec); CLT = clot lysis time (sec); CLS = clot lifespan (sec); [CORM-2] = μM of CORM-2 present.

TABLE 3

CLSM Values in Normal Plasma Following CORM-2 or iCORM-2 Exposure

| | 0 μM CORM-2 | 100 μM CORM-2 | 100 μM iCORM-2 |
|---|---|---|---|
| TMRTG | 185 (182, 188) | 155 (140, 172)* | 185 (172, 200)† |
| MRTG | 4.4 (4.0, 4.8) | 9.7 (8.2, 11.1)* | 5.3 (5.1, 5.5)*† |
| TTG | 132 (126, 140) | 281 (266, 290)* | 156 (142, 168)*† |
| TMRL | 340 (228, 402) | 1218 (974, 1370)* | 182 (168, 202)*† |
| MRL | −1.5 (−1.7, −1.3) | −1.9 (−2.2, −1.8)* | −3.1 (−3.4, −2.9)*† |
| CGT | 225 (218, 232) | 508 (490, 575)* | 225 (210, 235)† |
| CLT | 728 (582, 752) | 1768 (1578, 2085)* | 385 (368, 420)*† |
| CLS | 950 (787, 985) | 2325 (2152, 2530)* | 612 (582, 655)*† |

Data are presented as median (1$^{st}$, 3$^{rd}$ quartiles).
*P < 0.05 vs. 0 μM CORM-2,
†P < 0.05 vs. 100 μM CORM-2.

TABLE 4

CLSM in FXIII and PAI-1 Deficient Plasma Following CORM-2 Exposure

| | FXIII Deficient Plasma | | PAI-1 Deficient Plasma | |
|---|---|---|---|---|
| CORM-2 | − | + | − | + |
| TMRTG | 185 (178, 192) | 195 (190, 205) | 158 (145, 160) | 160 (155, 168) |
| MRTG | 1.1 (1.0, 1.2) | 5.8 (4.8, 6.6)* | 7.2 (6.8, 7.8) | 9.4 (8.4, 10.2)* |
| TTG | 39 (33, 43) | 160 (130, 177)* | 168 (152, 180) | 228 (205, 242)* |
| TMRL | 252 (242, 312) | 855 (648, 1068)* | 418 (330, 595) | 750 (632, 775)* |
| MRL | −0.4 (−0.5, −0.4) | −1.0 (−1.2, −0.9)* | −2.0 (−2.6, −1.8) | −2.2 (−2.4, −1.8) |
| CGT | 192 (175, 212) | 820 (652, 908)* | 290 (238, 358) | 500 (438, 588)* |
| CLT | 572 (505, 618) | 1460 (1245, 1698)* | 682 (568, 808) | 1070 (905, 1210)* |
| CLS | 775 (682, 820) | 2258 (1962, 2660)* | 1000 (790, 1170) | 1565 (1410, 1780)* |

Data are presented as median (1$^{st}$, 3$^{rd}$ quartiles). + CORM-2 = 100 μM concentration.
*P < 0.05 vs. − CORM-2 exposure.

TABLE 5

CLSM in TAFI and $\alpha_2$-Antiplasmin Deficient Plasma Following CORM-2 Exposure

| | TAFI Deficient Plasma | | $\alpha_2$-Antiplasmin Plasma | |
|---|---|---|---|---|
| CORM-2 | − | + | − | + |
| TMRTG | 172 (168, 180) | 175 (170, 185) | 162 (160, 165) | 160 (158, 162) |
| MRTG | 4.3 (4.0, 4.4) | 6.1 (5.9, 6.6)* | 7.5 (7.1, 8.5) | 10.1 (9.3, 10.3)* |
| TTG | 100 (96, 104) | 142 (140, 157)* | 202 (191, 226) | 231 (220, 250) |
| TMRL | 415 (348, 435) | 612 (592, 690)* | 62 (58, 68) | 68 (60, 82) |
| MRL | −1.3 (−1.4, −1.2) | −1.4 (−1.6, −1.3) | −10.4 (−11.2, −9.5) | −10.0 (−10.9, −9.3) |
| CGT | 272 (240, 305) | 410 (392, 458)* | 175 (170, 192) | 188 (175, 205) |
| CLT | 662 (558, 718) | 932 (912, 995)* | 155 (155, 165) | 190 (175, 210)* |
| CLS | 965 (790, 995) | 370 (1320, 1450)* | 332 (322, 355) | 378 (348, 410)* |

Data are presented as median (1$^{st}$, 3$^{rd}$ quartiles). + CORM-2 = 100 μM concentration.
*P < 0.05 vs. − CORM-2 exposure.

Discussion

CORM-2, in a concentration-dependent manner, enhances plasma clot formation and attenuates fibrinolysis. These phenomena appear to be driven by CO, as unlike the enhancement of coagulation observed with iCORM-2 in the absence of tPA (Example 1), iCORM-2 appears to, in some way, enhance tPA mediated fibrinolysis. Thus, in a fibrinolytic environment, it is CO, and not the carrier molecule, that is responsible for enhanced clot growth and attenuated fibrinolysis. This is particularly interesting, in that it appears that CO and iCORM-2 modify clot matrix formation in two different ways—both enhancing velocity of formation and clot strength, but only CO rendering the matrix less vulnerable to tPA mediated fibrinolysis.

With regard to the mechanism(s) by which CO attenuates fibrinolysis, the data indicate that there is a hierarchy of importance when considering the roles played by the antifibrinolytic proteins considered. Not to be bound by theory, the findings suggest that there was essentially no role played by FXIII, a relatively equivalent and moderate role played by PAI-1 and TAFI, and a critical role played by $\alpha_2$-antiplasmin in CORM-2 mediated diminution of fibrinolysis.

Example 3

Effects of Carbon Monoxide Releasing Agents on Thick Diameter Fibrin Fiber Formation Materials and Methods Thrombus Formation Protocol. Pooled normal plasma (George King Bio-Medical, Overland Park, Kans.) anticoagulated with sodium citrate was utilized for experimentation. As described in Examples 1 and 2, the lot of plasma had a prothrombin time (PT) of 12.7 seconds, an activated partial thromboplastin time (aPTT) of 29.6 seconds, and a fibrinogen concentration greater than 250 mg/dL. Factor XIII (FXIII) deficient plasma anticoagulated with sodium citrate was also obtained from the same vendor. The final volume for all subsequently described plasma sample mixtures was 359.4 µL. Sample composition consisted of 326 µL of plasma, 10 µL of tissue factor (0.1% final concentration in 0.9% NaCl; Diagnostica Stago, Asnieres, France), 3.6 µL of dimethyl sulfoxide (DMSO) or DMSO with CORM-2 (100 µM final concentration; Sigma-Aldrich, St. Louis, Mo.), and 20 µL of 200 mM $CaCl_2$. This concentration of CORM-2 was chosen because the concentration of CO released would be expected to be in the mid to lower ranges used in previously reported ex vivo, in vitro, and cell-based experiments (Motterlini et al. 2002, Megias et al. 2007, Chlopicki et al. 2006). Also, 0.75M of CO is released from every mole of CORM-2, with a CO release half-life of 1 min once placed in aqueous solution pH=7.4 at a temperature of 37° C. (Motterlini et al. 2005). Plasma sample mixtures were placed in a closed plastic tube for 15 min in a 37° C. water bath.

Electron Microscopy Sample Preparation and Examination Protocol. Following the 15 min incubation, thrombi were placed in fixative 2.5% glutaraldehyde/1% paraformaldehyde in 0.1M Sorenson's Phosphate Buffer pH 7.2 for 3 days. Portions of the samples were dissected into 3 mm×2 mm×1 mm planar sections and rinsed in $dH_2O$ overnight (O/N). The samples were washed with $dH_2O$ three times consecutively for 10 min followed by osmication with 1% $OsO_4$ at room temperature (RT) in the dark for 1.5 hrs. The osmication was performed for surface penetration and push-processed for internal penetration in a Pelco Biowave microwave 80 W (Redding, Calif.) for 90 sec on a 3 min off followed by 90 sec on cycle. Samples were then rinsed three times in $dH_2O$, followed by a 1% uranyl acetate stain en bloc for 4 hours at RT with three subsequent rinses in $dH_2O$. Alcohol dehydration steps consisted of 25%, 50%, 70%, 95%, 100% (twice), and 2 final dehydrations in propylene oxide (PO). All samples were subsequently microwaved at 150 W for 45 sec. The samples were then pre-infiltrated with Polybed 812 (EMS, Hatfield, Pa.) at a 1:1 resin/PO, microwaved for 4.5 min at 350W, and then washed in PO. Samples were then again infiltrated using fresh Polybed 812 O/N on a tissue rotator. The samples underwent another PO wash, were exposed to fresh Polybed 812 for 6 hours, and were placed in an embedding mold and polymerized at 65° C. for 18 hours. Samples were removed from the oven, passively cooled to RT, and cut using a diamond knife (Diatome Ultra EMS Hatfield, Pa.) on an ultra microtome (Leica Ultracut UCT, Leica Microsystems Inc., Bannockbum, Ill.). Sections were cut 0.1 micron thick and placed on copper 100 mesh grids (EMS Hatfield, Pa.). Images were acquired using a JEOL 1200 TEM (Peabody, Mass.) using an AMT XR40 digital camera (Advanced Microscope Technologies, Danvers, Mass.). Two regions of each thrombus were examined, with photographs of each region taken at 5000; 15,000; 30,000; and 60,000-fold magnification. Photos were representative of multiple views of each region.

Results

Figure 11:
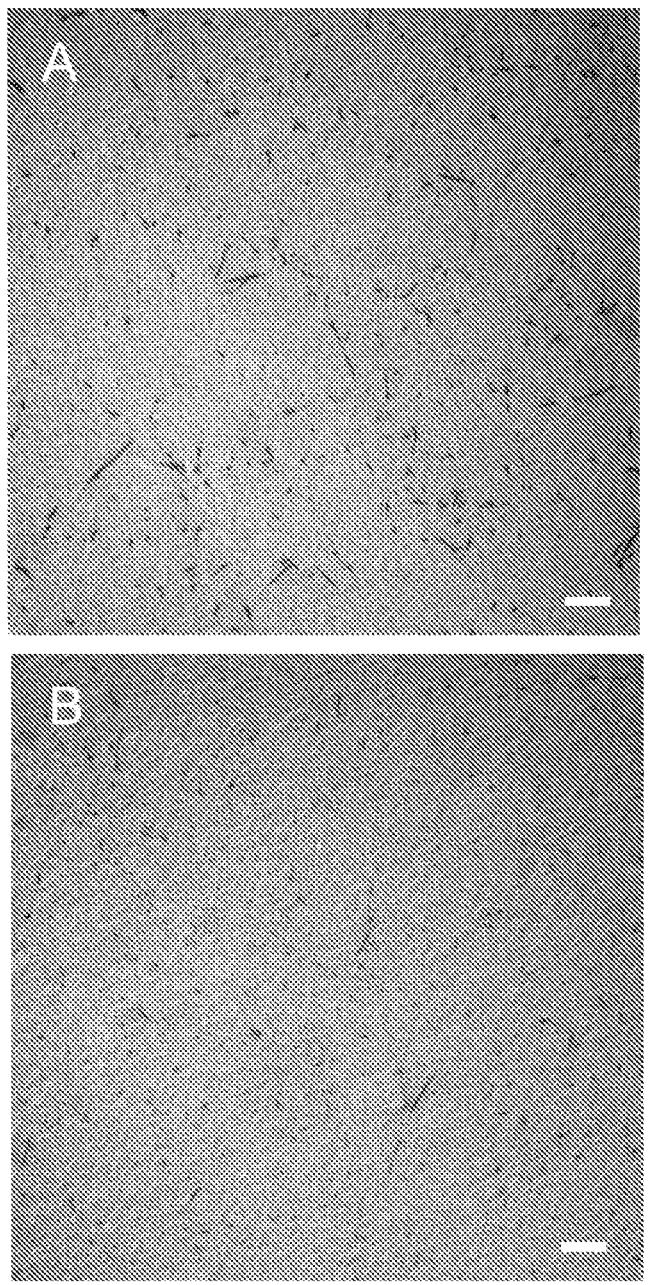
FIG. 11 contains pictures showing the effects of CORM-2 on normal plasma thrombus ultrastructure at low magnification. The magnification for both panels was 5,000-fold normal. Panel A shows normal plasma not exposed to CORM-2 and Panel B shows normal plasma exposed to 100 µM CORM-2. The white bar in the right bottom corner of both panels represents 2 micrometers. A difference between the two panels was the reduction of thick fiber formation following CORM-2 exposure.

Effects of CORM-2 in Normal Plasma. The ultrastructure of normal plasma thrombi exposed to either 0 or 100 µM CORM-2 are depicted at low magnification in FIG. 11 and high magnification in FIG. 12. At low magnification, there was a reduction in thick fiber formation following CORM-2 exposure. At the highest magnification, there was no remarkable difference in the thin fiber architecture noted. These observations were also noted in intermediate magnification views.

Figure 13:
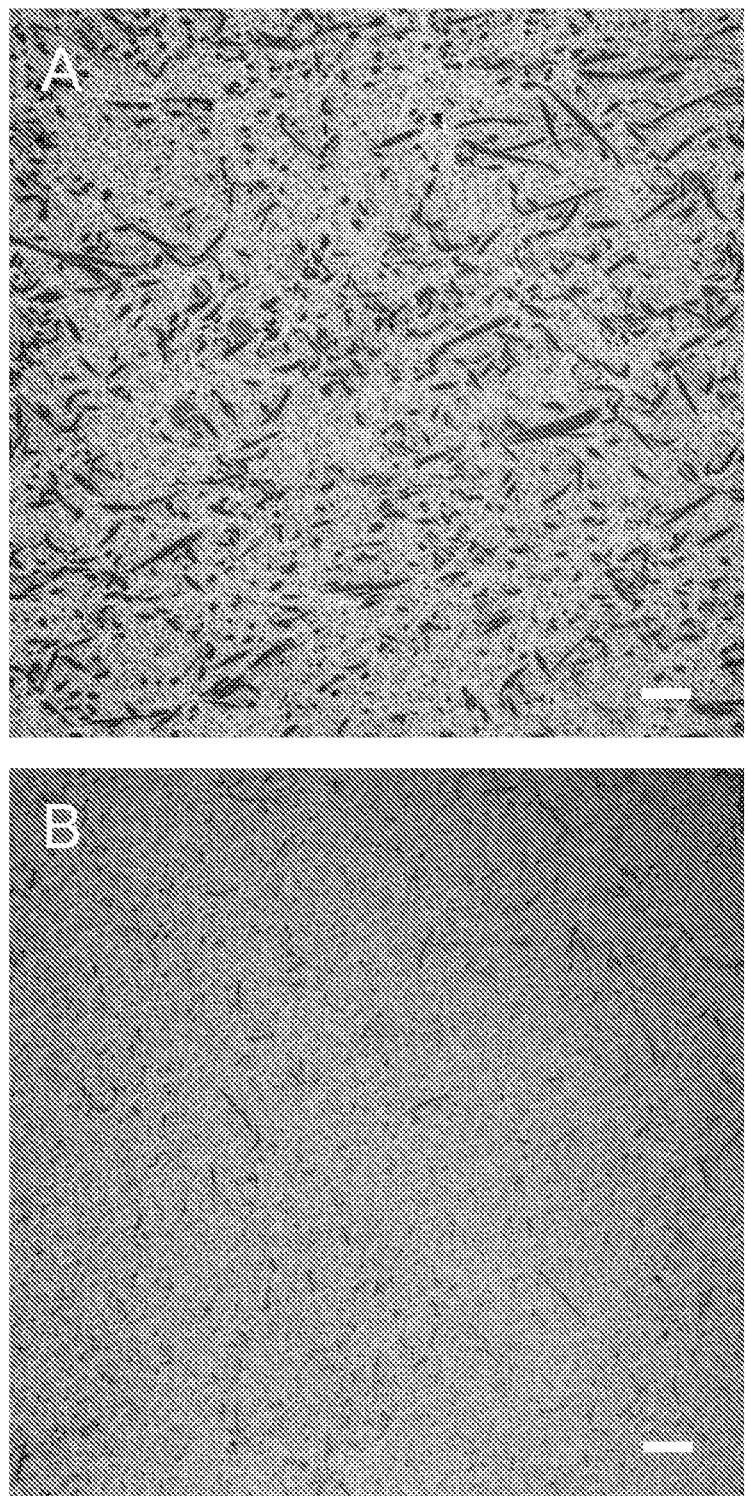
FIG. 13 contains pictures showing the effects of CORM-2 on FXIII-deficient plasma thrombus ultrastructure at low magnification. The magnification for both panels was 5,000-fold normal. Panel A shows FXIII-deficient plasma not exposed to CORM-2 and Panel B shows FXIII-deficient plasma exposed to 100 μM CORM-2. The white bar in the right bottom corner of both panels represents 2 micrometers. CORM-2 exposure decreased thick fiber formation and increased thin fiber matrix content in FXIII-deficient clot. When compared to Panel A in FIG. 11, CORM-2 exposure "normalized" thrombus ultrastructure in FXIII-deficient plasma as depicted in Panel B of this figure.
Figure 14:
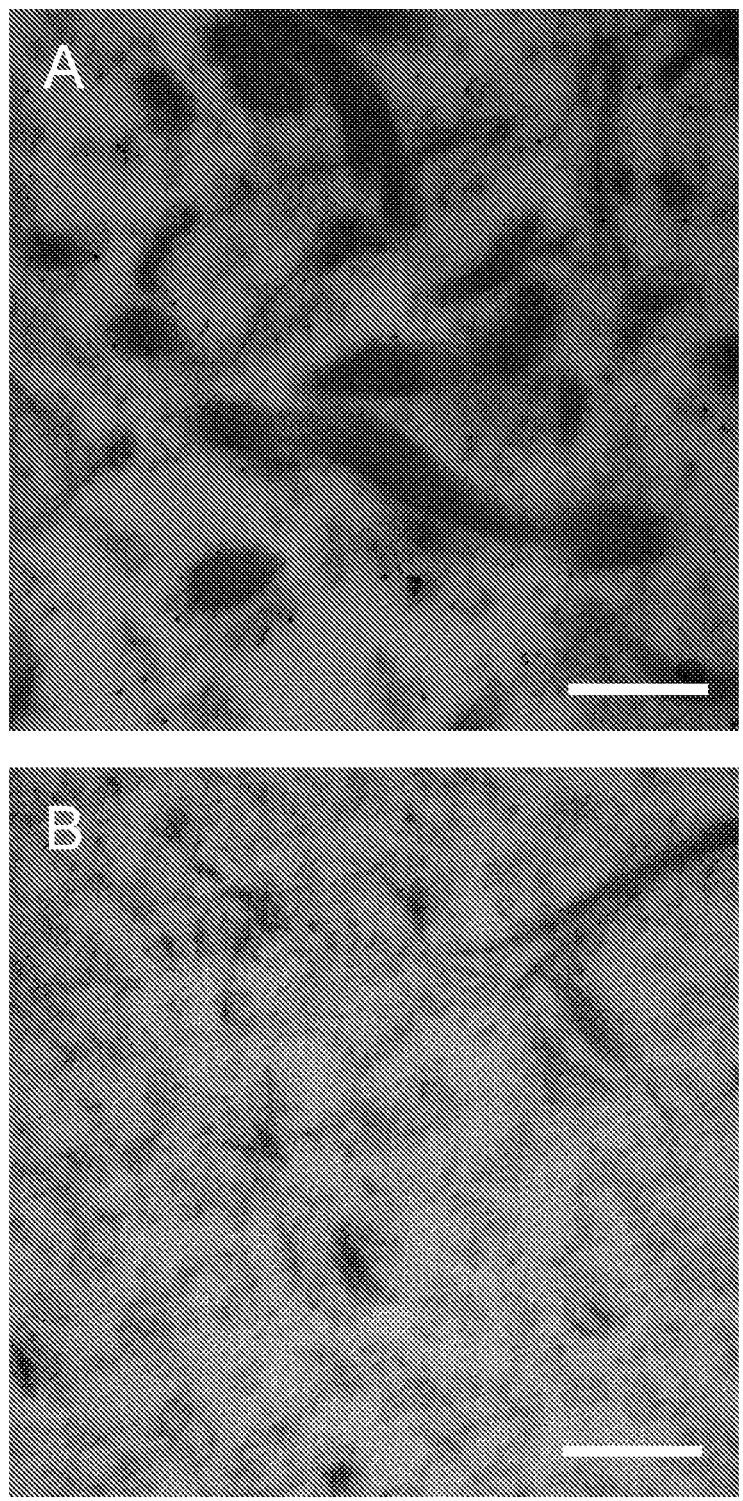
FIG. 14 contains pictures showing the effects of CORM-2 on FXIII-deficient plasma thrombus ultrastructure at high magnification. The magnification for both panels was 60,000-fold normal. Panel A shows FXIII-deficient plasma not exposed to CORM-2 and Panel B shows FXIII-deficient plasma exposed to 100 μM CORM-2. The white bar in the right bottom corner of both panels represents 500 nanometers. CORM-2 exposure decreased thick fiber content and enhanced thin fiber clot formation.

Effects of CORM-2 in FXIII-deficient Plasma. The ultrastructure of FXIII-deficient plasma thrombi exposed to either 0 or 100 µM CORM-2 are depicted at low magnification in FIG. 13 and high magnification in FIG. 14. At low magnification, there was a reduction in thick fiber formation coupled with enhanced fine fiber content following CORM-2 exposure. The ultrastructure of normal plasma thrombus not exposed to CORM-2 (FIG. 11, panel A), appeared very similar to FXIII-deficient plasma clot exposed to CORM-2 (FIG. 13, panel B). At the highest magnification, there was an increase in the thin fiber architecture noted in FXIII-deficient plasma thrombus following CORM-2 exposure. These observations in FXIII-deficient were also noted in the intermediate magnification views.

Discussion

Figure 12:
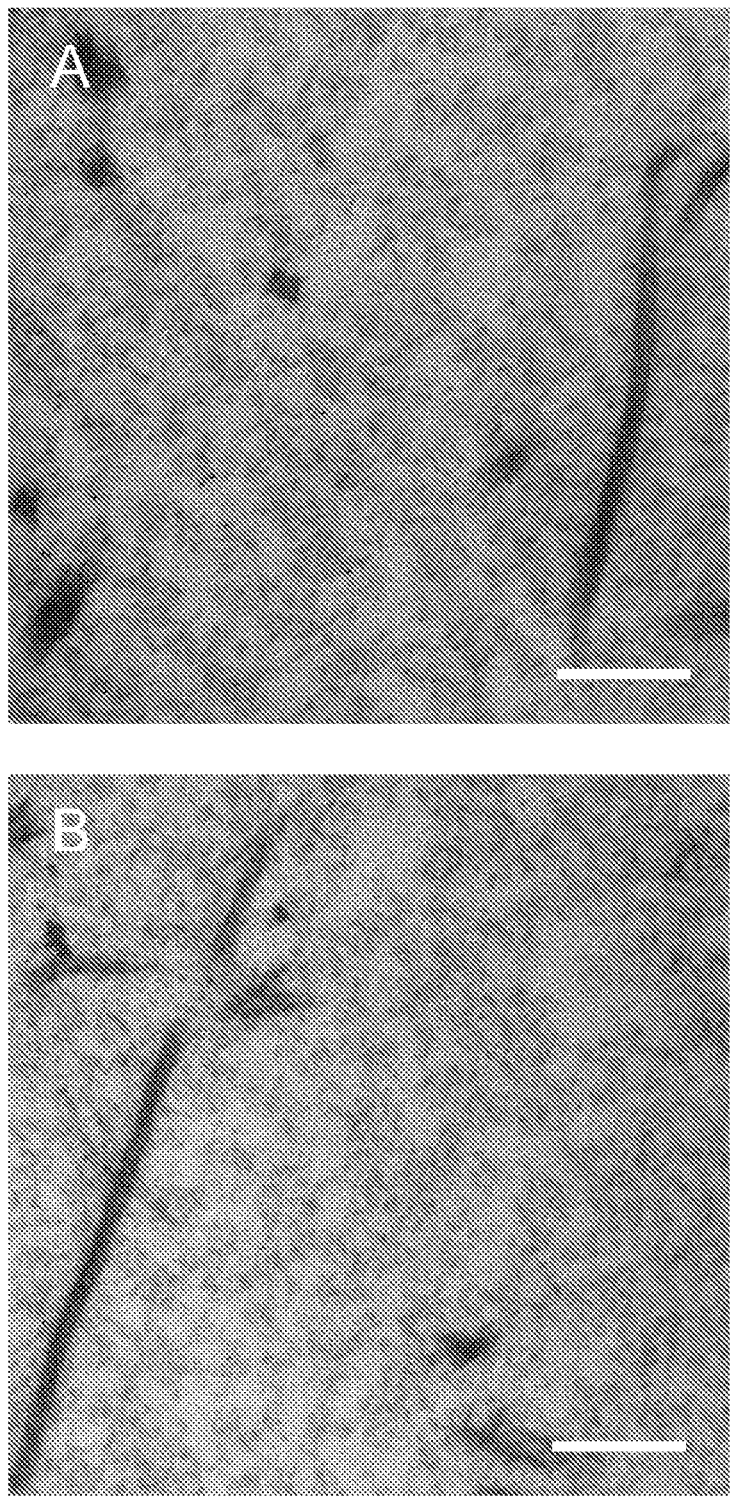
FIG. 12 contains pictures showing the effects of CORM-2 on normal plasma thrombus ultrastructure at high magnification. The magnification for both panels was 60,000-fold normal. Panel A shows normal plasma not exposed to CORM-2 and Panel B shows normal plasma exposed to 100 μM CORM-2. The white bar in the right bottom corner of both panels represents 500 nanometers. There was little difference in thin fiber architecture following CORM-2 exposure.

CORM-2 exposure attenuated thick fiber formation in both normal and FXIII-deficient plasma. Also, CORM-2 enhanced fine fiber formation in FXIII-deficient plasma. When considered together, the CORM-2 mediated changes in fiber type explain the viscoelastic differences noted in Examples 1 and 2, given that fine fiber formation enhanced clot strength and diminished fibrinolytic vulnerability. CORM-2 mediated changes in thin fiber formation were most conspicuous in FXIII-deficient plasma, especially at high magnification (FIG. 14) as compared to normal plasma (FIG. 12). These data showed that CORM-2/CO promoted a change in thrombus ultrastructure consistent with the enhanced speed of formation, increased strength, and improved fibrinolytic resistance of CORM-2 exposed thrombi as described in Examples 1 and 2.

Example 4

Effects of Carbon Monoxide Releasing Agents on the Velocity of Thrombus Growth and Strength in Hemophilia A, Hemophilia B, and Factor VII Deficient Plasmas

Materials and Methods

Plasma deficient (<1% normal activity) in factor VIII (FVIII; 11 individuals), factor IX (FIX; 5 individuals), or factor VII (FVII; 4 individuals) was obtained from anonymous donors (George King Bio-Medical, Overland Park, Kans.) and was anticoagulated with sodium citrate. The final volume for all subsequently described plasma sample mixtures was 359.4 mL. Sample composition consisted of 326 mL of plasma, 10 mL of tissue factor (0.1% final concentration in 0.9% NaCl; Diagnostica Stago, Asnieres, France), 3.6 mL of dimethyl sulfoxide (DMSO) or DMSO with CORM-2 (100 mmol final concentration; Sigma-Aldrich, St. Louis, Mo.), and 20 mL of 200 mmol $CaCl_2$. This concentration of CORM-2 was chosen because the concentration of carbon monoxide released would be expected to be in the mid to lower ranges used in Example 1 and previously reported ex vivo, in-vitro, and cell-based experiments (Motterlini et al. 2002; Megias et al. 2007; Chlopicki et al. 2006). Also, 0.75 mol of carbon monoxide is released from every mole of CORM-2, with a carbon monoxide release half-life of 1 min once placed in aqueous solution pH=7.4 at a temperature of 37° C. (Motterlini et al. 2005). While CORM-2 decays slowly in DMSO, DMSO was added to the dry compound just prior to placement into the plasma mixture.

Plasma sample mixtures were placed in a disposable cup in a computer-controlled THROMBELASTOGRAPH® hemostasis system (Model 5000; Haemoscope Corp., Niles, Ill.), with addition of $CaCl_2$ as the last step to initiate clotting. Data were collected until clot strength stabilized (maximum amplitude). The following variables described in Example 1 were determined at 37° C.: Time to maximum rate of thrombus generation (TMRTG, the time interval (sec) observed prior to maximum speed of clot growth); Maximum rate of thrombus generation (MRTG, the maximum velocity of clot growth observed (dynes/$cm^2$/sec)); Total thrombus generation (TTG, the total area under the velocity curve during clot growth (dynes/$cm^2$), representing the amount of clot strength generated during clot growth).

Statistical analyses. Each individual thrombelastographic parameter response to CORM-2 exposure was graphically displayed, and data derived from the FVIII deficient cohort was also presented as mean±SD. A paired student's t-test was used to analyze the effects of CORM-2 exposure in FVIII deficient individuals. The results of the FIX and FVII deficient groups were presented but not statistically analyzed secondary to the small number of individuals in each cohort. Additionally, the data were compared with results obtained with pooled normal plasma (George King Bio-Medical) under identical experimental circumstances (Example 1). The lot of plasma had a prothrombin time of 12.7 s, an activated partial thromboplastin time of 29.6 s, and a fibrinogen concentration greater than 250 mg/dL. Statistical analyses and graphical representation of the data were generated with commercially available software (SigmaPlot 11.0; Systat Software Inc., San Jose, Calif.; CorelDRAW 12.0; Corel Corp., Ottawa, Ontario, Canada). A P value of less than 0.05 was considered significant.

Results

Effects of carbon monoxide releasing molecules-2 in factor VIII deficient plasma. There was no significant difference in TMRTG values between samples exposed to 0 mmol (4.3±2.2 min) and 100 mmol (4.0±2.3 min) CORM-2. However, MRTG values were increased from 2.7±1.4 dynes/$cm^2$/sec in samples not exposed to CORM-2 to 5.0±2.7 dynes/$cm^2$/sec after exposure to 100 mmol CORM-2. TTG values were increased from 156±46 dynes/$cm^2$ in samples not exposed to CORM-2 to 232±56 dynes/$cm^2$ after exposure to 100 mmol CORM-2. Individual responses to CORM-2 exposure are displayed in FIG. 15. CORM-2 enhanced the speed of clot formation and strength.

Effects of carbon monoxide releasing molecule-2 in factor IX deficient plasma. As displayed in FIG. 16, CORM-2 exposure decreased the TMRTG value of all five individual plasma samples tested. With regard to MRTG, four of five individuals had an increase in the speed of clot formation following exposure to CORM-2, but one individual demonstrated a small decrease in MRTG. All individual plasma samples demonstrated an increase in TTG following CORM-2 exposure.

Figure 17:
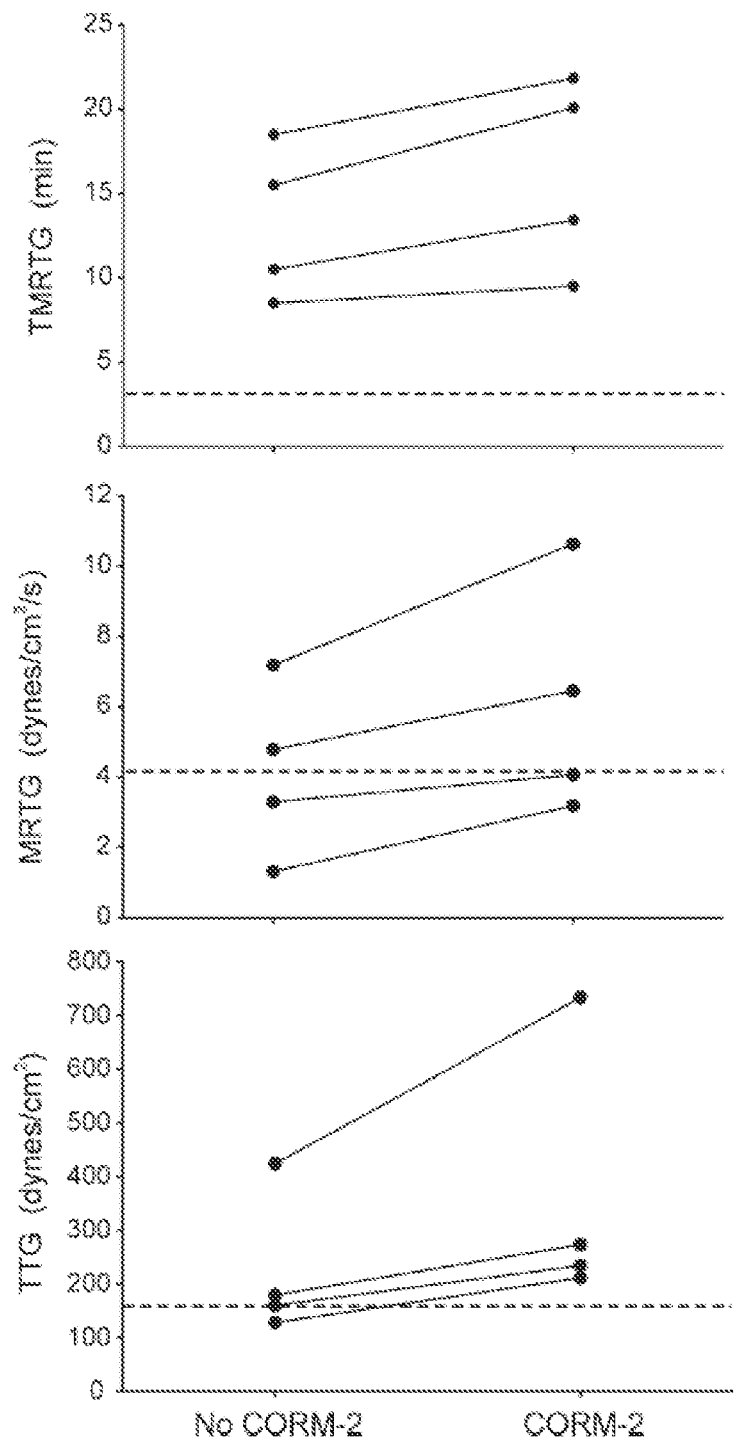
FIG. 17 shows coagulation kinetics in factor VII deficient plasma samples exposed to CORM-2 and not exposed to CORM-2 (control). Compared with control conditions, individual plasma samples exposed to 100 mmol CORM-2 had an increase in both the velocity of clot formation (MRTG) and clot strength (TTG). All four individuals deficient in FVII demonstrated a prolongation of the TMRTG following CORM-2 exposure. The dashed line represents the mean value for pooled normal plasma following tissue factor activation.

Effects of carbon monoxide releasing molecule-2 in factor VII deficient plasma. As depicted in FIG. 17, exposure to CORM-2 resulted in an increase in TMRTG in all individuals tested. Conversely, CORM-2 exposure resulted in an increase in MRTG and TTG in all FVII deficient plasma donors. Thus, CORM-2 exposure paradoxically delayed the onset of maximum velocity of clot growth but nevertheless enhanced the speed of clot formation and strength.

Discussion

Figure 15:
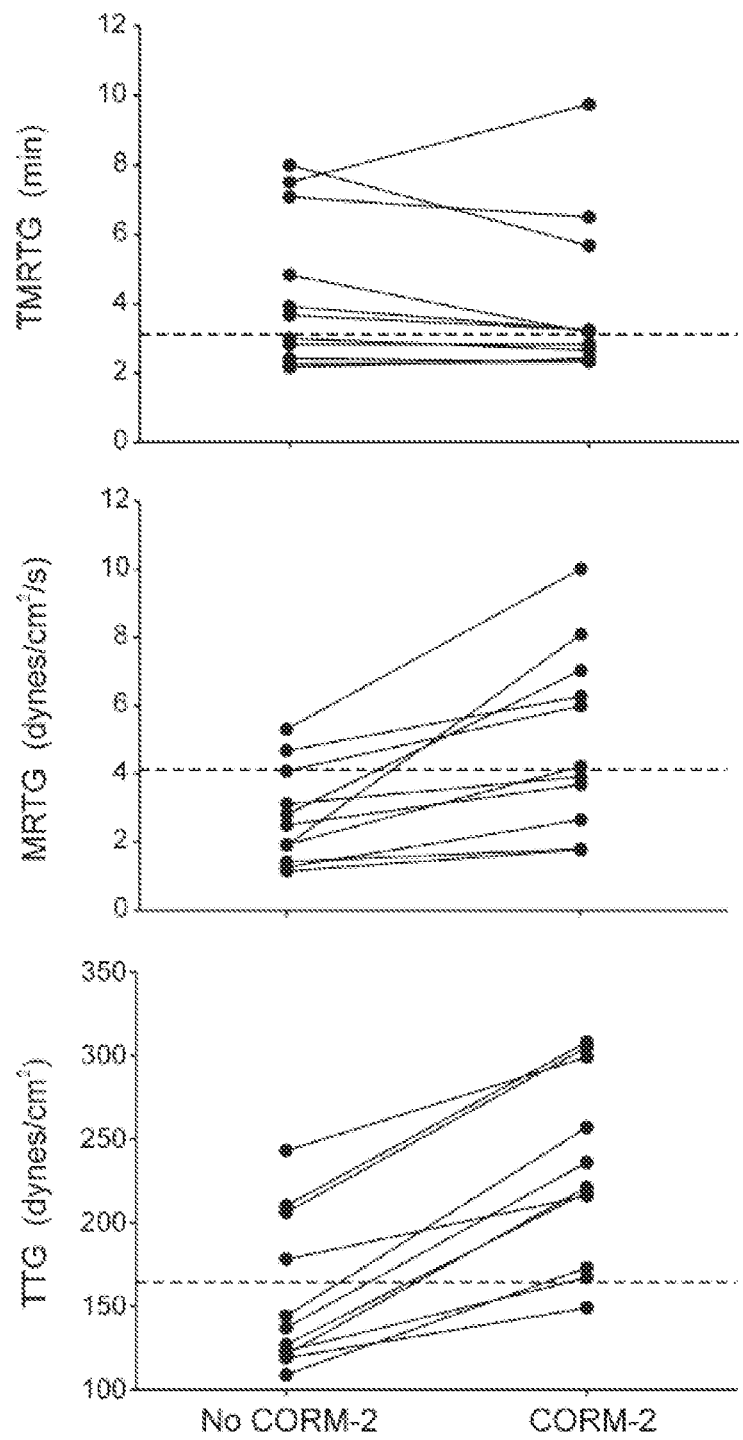
FIG. 15 shows coagulation kinetics in factor VIII deficient plasma samples exposed to CORM-2 and not exposed to CORM-2 (control). Compared with control conditions, individual plasma samples exposed to 100 mmol CORM-2 had significant increases in both the velocity of clot formation (MRTG) and clot strength (TTG) without change in TMRTG. The dashed line represents the mean value for pooled normal plasma following tissue factor activation.
Figure 16:
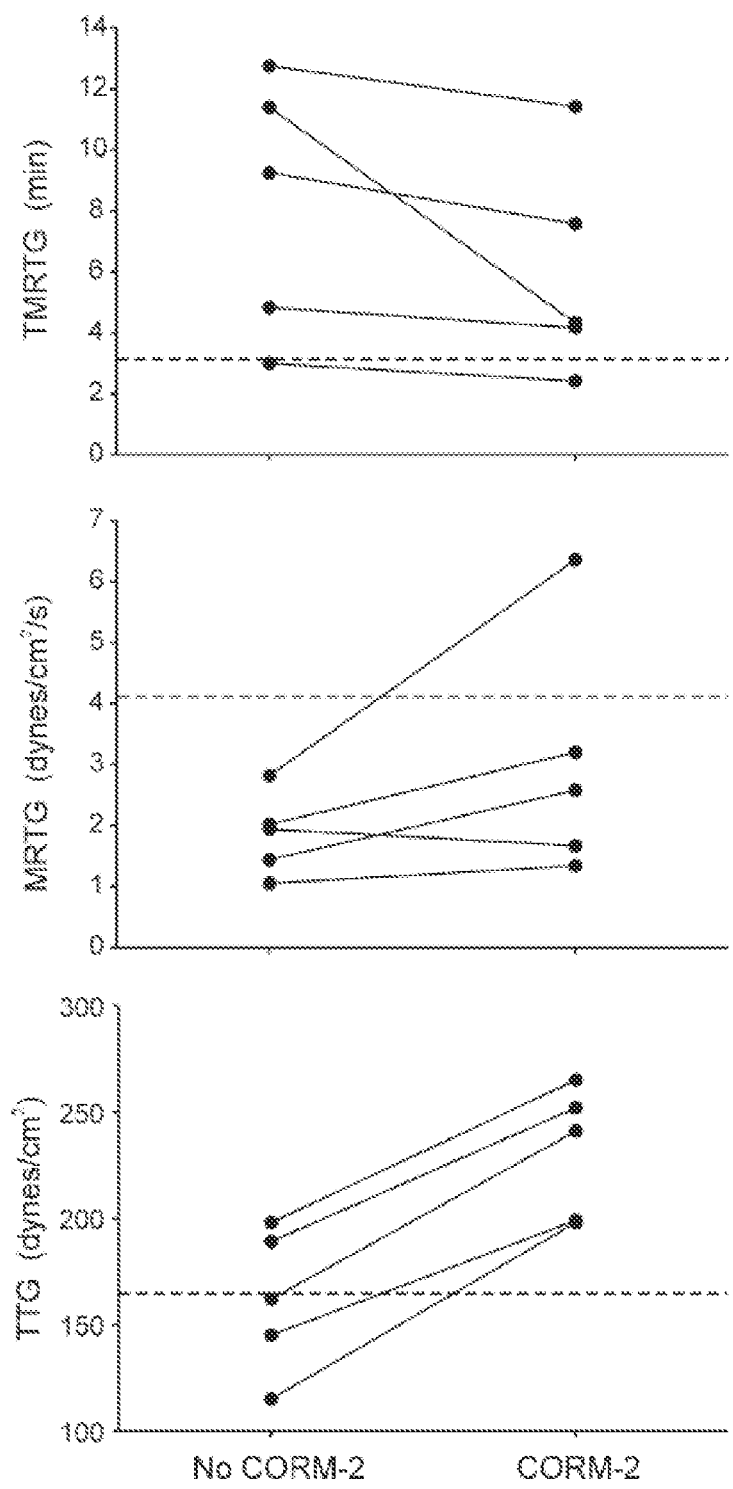
FIG. 16 shows coagulation kinetics in factor IX deficient plasma samples exposed to CORM-2 and not exposed to CORM-2 (control). Compared with control conditions, individual plasma samples exposed to 100 mmol CORM-2 had an increase in both the velocity of clot formation (MRTG, four of five donors) and clot strength (TTG, five of five donors). All five donors demonstrated a decrease in the TMRTG following CORM-2 exposure. The dashed line represents the mean value for pooled normal plasma following tissue factor activation.

CORM-2 enhanced coagulation in plasma obtained from FVIII, FIX, and FVII deficient anonymous donors. As with normal or factor XIII deficient plasma (Example 1), CORM-2 enhanced the velocity of formation and strength of FVIII, FIX, and FVII deficient plasma. In addition to serving as a 'proof of concept' that CORM-2 could be used as a hemostatic agent to treat hemophiliac-related bleeding, these data support the conclusion that carbon monoxide/CORM-2 modifies fibrinogen prior to thrombin-mediated polymerization. CORM-2 releases carbon monoxide with a half-life of 1 min, and as seen in FIGS. 15-17, the enhancement of the velocity of formation and increase in strength associated with CORM-2 occurred more than 20 half-lives after exposure to the compound. Given that carbon monoxide rapidly diffuses through plasma, these data support the concept that carbon monoxide released from CORM-2 modifies fibrinogen to improve coagulation kinetics. In summary, CORM-2 generally improved the velocity of formation and strength in the deficient plasmas tested.

Example 5

Effects of Carbon Monoxide Releasing Agents in Rat and Rabbit Plasma

Materials and Methods

Two sets of two Sprague Dawley outbred male rats were anesthetized with ketamine and xylazine and had blood drawn via cardiac puncture, pooled in two batches, and anticoagulated 1:9 with 3.2% sodium citrate. Two male New Zealand White rabbits were sedated with acepromazine and had blood collected via central ear artery and similarly anticoagulated. Blood was centrifuged at 3000×g for 15 min, and the plasma stored in two batches until analyzed. The final volume for thrombelastographic plasma sample mixtures was 359.6 µL. Sample composition consisted of 316 µL of plasma; 10 µL of tissue factor reagent (0.1% final concentration in $dH_2O$; Instrumentation Laboratory, Lexington, Mass.); 10 µL of $dH_2O$ or tissue-type plasminogen activator (tPA, 580 U/μg, Genentech, Inc., San Francisco, Calif.) for a final activity of 2000 U/mL for rat plasma or 300 IU/mL for rabbit plasma; 3.6 μL of dimethyl sulfoxide (DMSO) or DMSO with CORM-2 (100 μM final concentration; Sigma-Aldrich, St. Louis, Mo.); and 20 μL of 200 mM $CaCl_2$. The tPA activity for each species was determined with pilot data to obtain reproducible lysis within 15 min. There was no appreciable lysis in rat plasma at 100, 300, or 1000 U/mL tPA. Plasma sample mixtures were placed in a disposable cup in a computer-controlled THROMBELASTOGRAPH® hemostasis system (Model 5000, Haemoscope Corp., Niles, Ill.), with addition of $CaCl_2$ as the last step to initiate clotting. In experiments without tPA, data were collected until clot strength (maximum amplitude) was stable. In experiments with tPA, data derived from the second rabbit plasma samples were collected for 60 min whereas data obtained with the second rat plasma samples were collected for 15 min. Thrombelastographic variables were determined at 39° C. as previously described in Examples 1, 2, and 4. Data were statistically compared with unpaired Student's t-test.

Results

Figure 18:
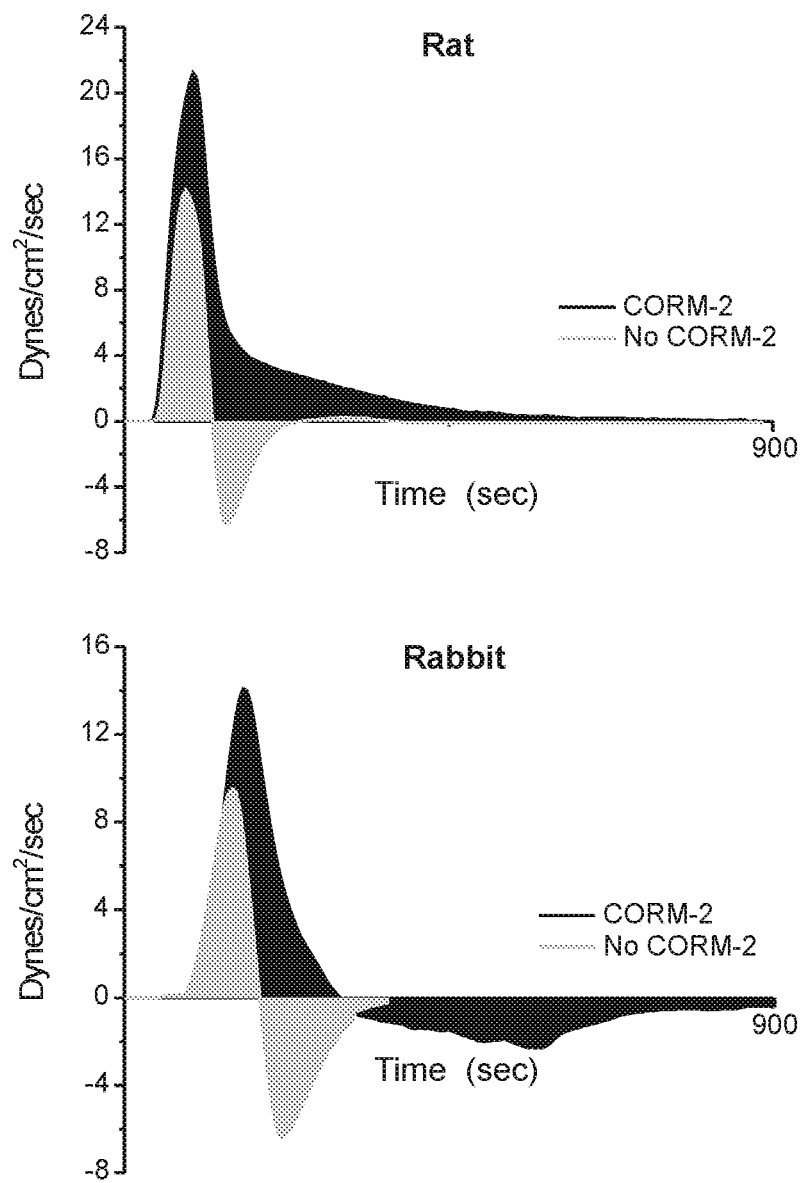
FIG. 18 is a graph showing the effect of CORM-2 on rat and rabbit thrombus formation with tPA present. Top panel: exposure of rat plasma to 100 μM CORM-2 (black trace) resulted in improved velocity of growth, strength, and no fibrinolysis compared to unexposed plasma (gray trace). Bottom panel: exposure of rabbit plasma to 100 μM CORM-2 (black trace) resulted in improved velocity of growth and strength, with prolonged onset of fibrinolysis compared to unexposed plasma (gray trace).

As shown in Table 6, CORM-2 exposure significantly increased the velocity of clot formation and strength in rat and rabbit plasma with or without tPA addition. With regard to lysis, CORM-2 exposure completely inhibited lysis in rat plasma. In contrast, CORM-2 exposure significantly prolonged the onset of lysis and significantly decreased the rate of lysis in rabbit plasma. A representative pair of thrombelastograms with and without CORM-2 exposure in rat and rabbit plasma following tPA addition are displayed in FIG. 18.

TABLE 6

Thrombelastographic Values in Rat and Rabbit Plasma.

| | 0 μM CORM-2 | 100 μM CORM-2 | Percent Change |
|---|---|---|---|
| Rat (n = 4 experiments, no tPA) | | | |
| TMRTG | 1.5 ± 0.0 | 1.5 ± 0.1 | 0% |
| MRTG | 11.4 ± 0.7 | 14.7 ± 0.6* | 29% |
| TTG | 188 ± 6 | 230 ± 6* | 23% |
| Rabbit (n = 7 experiments, no tPA) | | | |
| TMRTG | 2.7 ± 0.4 | 2.8 ± 0.1 | 5% |
| MRTG | 9.5 ± 1.1 | 13.9 ± 2.9* | 46% |
| TTG | 232 ± 29 | 290 ± 35* | 25% |
| Rat (n = 4 experiments, 2000 U/ml tPA) | | | |
| TMRTG | 1.5 ± 0.0 | 1.5 ± 0.1 | 0% |
| MRTG | 11.4 ± 0.7 | 14.7 ± 0.6* | 29% |
| TTG | 188 ± 6 | 230 ± 6* | 23% |
| TMRL | 0.9 ± 0.0 | No Lysis | — |
| MRL | −11.2 ± 1.0 | 0.0 ± 0.0* | −100% |
| ACL | 117 ± 11 | 0 ± 0* | −100% |
| Rabbit (n = 4 experiments, 300 U/ml tPA) | | | |
| TMRTG | 2.5 ± 0.0 | 2.8 ± 0.1* | 8% |
| MRTG | 9.4 ± 0.3 | 14.2 ± 1.4* | 52% |
| TTG | 109 ± 2 | 237 ± 8* | 118% |
| TMRL | 1.2 ± 0.0 | 2.6 ± 0.5* | 110% |
| MRL | −6.6 ± 0.2 | −2.5 ± 0.4* | −63% |
| ACL | 101 ± 2 | 196.3 ± 25* | 94% |

Data are presented as mean ± SD. TMRTG = time to maximum rate of thrombus generation (min); MRTG = maximum rate of thrombus generation ($dynes/cm^2/sec$); TTG = total thrombus generation ($dynes/cm^2$); TMRL = time to maximum rate of lysis (min); MRL = maximum rate of lysis ($-dynes/cm^2/sec$); ACL = area under the curve of lysis ($-dynes/cm^2$).
*$P < 0.05$ vs. 0 μM CORM-2.

In conclusion, both rat and rabbit plasma displayed both procoagulant and antifibrinolytic responses to CORM-2 exposure. The plasmatic response of the rabbit to CORM-2 in the presence of fibrinolytic stress was more similar to that observed with humans (Example 2) as compared to the response noted in rat plasma.

Example 6

Effects of Carbon Monoxide Releasing Agents in Plasma Samples Collected from Subjects Exposed to Warfarin Materials and Methods Pooled normal plasma (George King Bio-Medical, Overland Park, Kans.) anticoagulated with sodium citrate was utilized for experimentation. The lot of plasma had a prothrombin time of 12.8 seconds, international normalized ratio (INR) value of 1.0, an activated partial thromboplastin time of 29.4 seconds, and a fibrinogen concentration of 310 mg/dL. Plasma anticoagulated with sodium citrate procured from anonymous donors treated with warfarin was also obtained from the same vendor. In the first series of experiments involving exposure of plasma to CORM-2 without concurrent exposure to tissue-type plasminogen activator (tPA, 580 U/μg, Genentech, Inc., San Francisco, Calif.), the INR values of donor samples were 1.5, 1.9 (2 donors), 2.0 (2 donors), 2.1, 2.2 (2 donors), 2.4, 3.6, 4.0, and 5.4. In the second series of experiments involving exposure to tPA, the INR values of plasma samples were 1.5, 2.0 (2 donors), 2.1, 2.4, 3.6, 4.0, and 5.4.

Plasma sample composition of experiments without tPA addition. The final volume for all subsequently described plasma sample mixtures was 359.6 μL. Sample composition consisted of 326 μL of plasma, 10 μL of tissue factor reagent (0.1% final concentration in $dH_2O$; Instrumentation Laboratory, Lexington, Mass.), 3.6 μL of dimethyl sulfoxide (DMSO) or DMSO with CORM-2 (100 μM final concentration; Sigma-Aldrich, St. Louis, Mo.), and 20 μL of 200 mM $CaCl_2$. Tissue factor stock was kept on ice prior to use and was remade every two hours. The concentration of CORM-2 used was that associated with maximal effect on coagulation and fibrinolysis in this system (Example 2). DMSO was added to dry CORM-2 just prior to placement into the plasma mixture. Six replicate experiments were performed with pooled normal plasma with or without CORM-2 added, whereas plasma obtained from subjects treated with warfarin underwent singlicate experiments with or without CORM-2 exposure.

Plasma sample composition of experiments with tPA addition. As in the series of experiments without tPA addition, the final volume of plasma sample mixtures was 359.6 μL. Sample composition consisted of 316 μL of plasma; 10 μL of tissue factor reagent (0.1% final concentration); 3.6 μL of DMSO without or with CORM-2 (100 μM final concentration); 10 μL of tPA diluted with 10 mM potassium phosphate buffer (pH 7.4) for a final activity of 100 IU/mL; and 20 μL of 200 mM $CaCl_2$. As with tissue factor reagent, tPA stock was kept on ice prior to use and was remade every two hours. Six replicate experiments were performed with pooled normal plasma with or without CORM-2 added, whereas plasma obtained from subjects treated with warfarin underwent singlicate experiments with or without CORM-2 exposure.

Clot Lifespan Model Analyses. Plasma sample mixtures were placed in a disposable cup in a computer-controlled THROMBELASTOGRAPH® hemostasis system (Model 5000, Haemoscope Corp., Niles, Ill.), with addition of $CaCl_2$ as the last step to initiate clotting. In the first series of experiments, no tPA was added and data were collected until clot strength (maximum amplitude) was stable. In the second series of experiments in which tPA was added, data were collected until clot lysis time occurred. The following variables were determined at 37° C. depending on whether or not tPA was present in the reaction mixture: Clot growth time (CGT, time from clot amplitude of 2 mm [102 dynes/cm$^2$] until maximum strength is achieved, in sec), Clot lysis time (CLT, time from when maximum strength was observed to 2 mm amplitude, in sec) and Clot lifespan (CLS, the sum of CGT and CLT). Additional elastic modulus-based parameters previously described in Examples 1-4 were determined. The nomenclature used to describe these phenomena is as follows: Time to maximum rate of thrombus generation (TMRTG): This is the time interval (sec) observed prior to maximum speed of clot growth. Maximum rate of thrombus generation (MRTG): This is the maximum velocity of clot growth observed (dynes/cm$^2$/sec). Total Thrombus Generation (TTG): This is the total area under the velocity curve during clot growth (dynes/cm$^2$), representing the amount of clot strength generated during clot growth. Time to maximum rate of lysis (TMRL): This is the time interval (sec) measured from the time of maximum strength to the time when the velocity of clot disintegration is maximal. Maximum Rate of Lysis (MRL): This is the maximum velocity of clot disintegration observed (—dynes/cm$^2$/sec). Area of Clot Lysis (ACL): This is the total area under the velocity curve during clot disintegration (–dynes/cm$^2$), representing the amount of clot strength lost during clot disintegration. As this model involves complete fibrinolysis, TTG is equivalent to ACL, so ACL was not presented as it provides no additional information.

Statistical Analyses. Data obtained from pooled normal plasma are presented as mean±SD. Analyses of the effects of CORM-2 on thrombelastographic variables obtained from pooled normal plasma were conducted using two-tailed, unpaired Student's t-tests. A P value of <0.05 was considered significant. Graphical representation of the thrombelastographic data derived from warfarin-treated subjects' plasma was generated with commercially available software (SigmaPlot 11.0, Systat Software, Inc., San Jose, Calif.). No statistical analyses of data obtained from warfarin-treated subjects were performed given the multiple INR values tested.

Results

Experiments without tPA addition. As shown in Table 7, exposure of normal plasma to CORM-2 decreased the time to maximum velocity of clot growth, increased the rate of clot growth, and increased clot strength. The mean value for each parameter derived from this data set is represented by a horizontal bar in FIG. 19.

Figure 19:
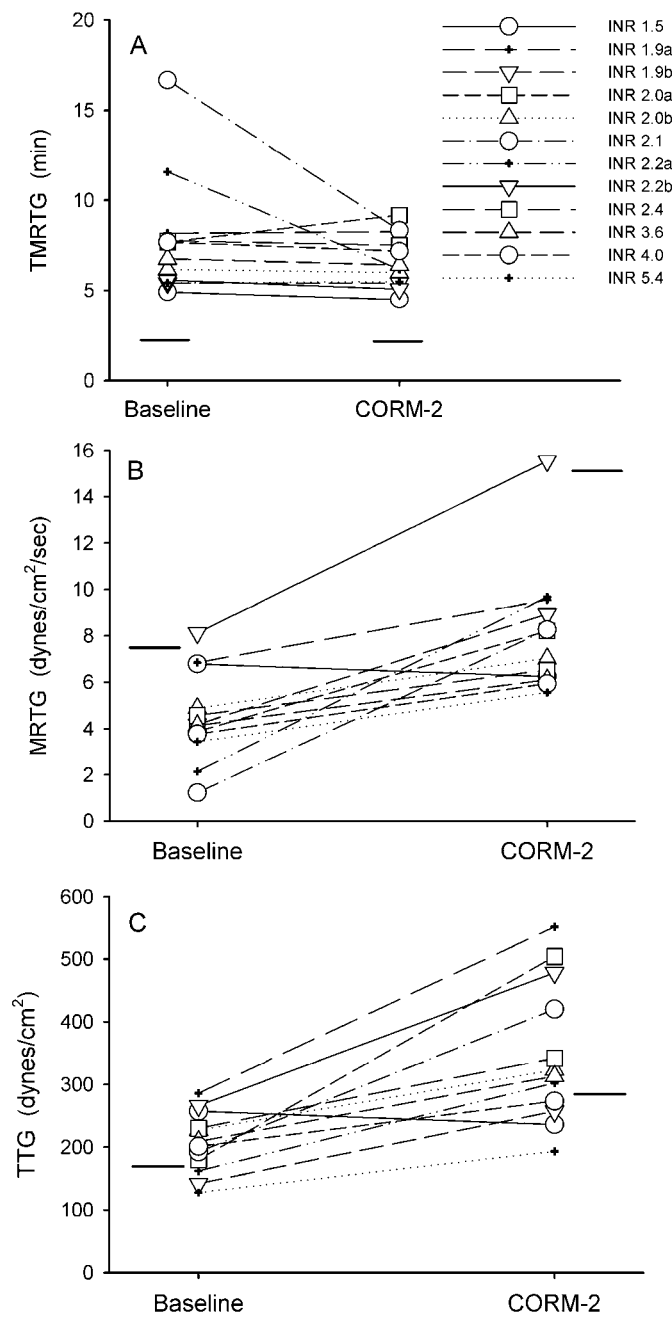
FIG. 19 is a graph showing the effect of CORM-2 on thrombus formation without tissue-type plasminogen activator (tPA) present. Baseline=0 μM CORM-2; CORM-2=100 μM CORM-2. Individual subjects are identified according to the legend in panel A. The short horizontal bars represent the mean value derived from normal human plasma with INR=1.0.

The data derived from subjects with INR values of 1.5-5.4 are displayed in FIG. 19. In panel A, CORM-2 exposure was associated with changes in TMRTG of −50% to 20% of baseline values. Of interest, all TMRTG values were greater than the mean values of normal plasma. In panel B, all but one subject (INR 1.5) had an increase in MRTG of 40% to 577% of baseline values. Nearly identical results were obtained from the subject with INR 1.5 when a second plasma sample was tested. While these increases were impressive, it is important to note that only one subject (INR 2.2) had an increase in MRTG value secondary to CORM-2 exposure that was similar to that noted with normal plasma. As displayed in panel C, CORM-2 exposure increased TTG values in all but one subject (INR 1.5), with values increased 42% to 180% of baseline values. In contrast to the MRTG data, the majority of subjects had a normal to supernormal increase in clot strength in response to CORM-2 exposure.

Experiments with tPA addition. In the presence of tPA, CORM-2 did not significantly decrease TMRTG, but did increase MRTG and TTG in a fashion similar to that seen in the absence of tPA (Table 7). The time to onset of maximum rate of lysis was increased with CORM-2, while paradoxically the maximum rate of lysis was also enhanced. Nevertheless, all phases of the clot lifespan were increased by CORM-2 exposure, resulting in a longer-lived thrombus. As with the previous dataset, the mean value for each parameter derived from normal plasma exposed to tPA is represented by a horizontal bar in FIGS. 20-22.

Figure 20:
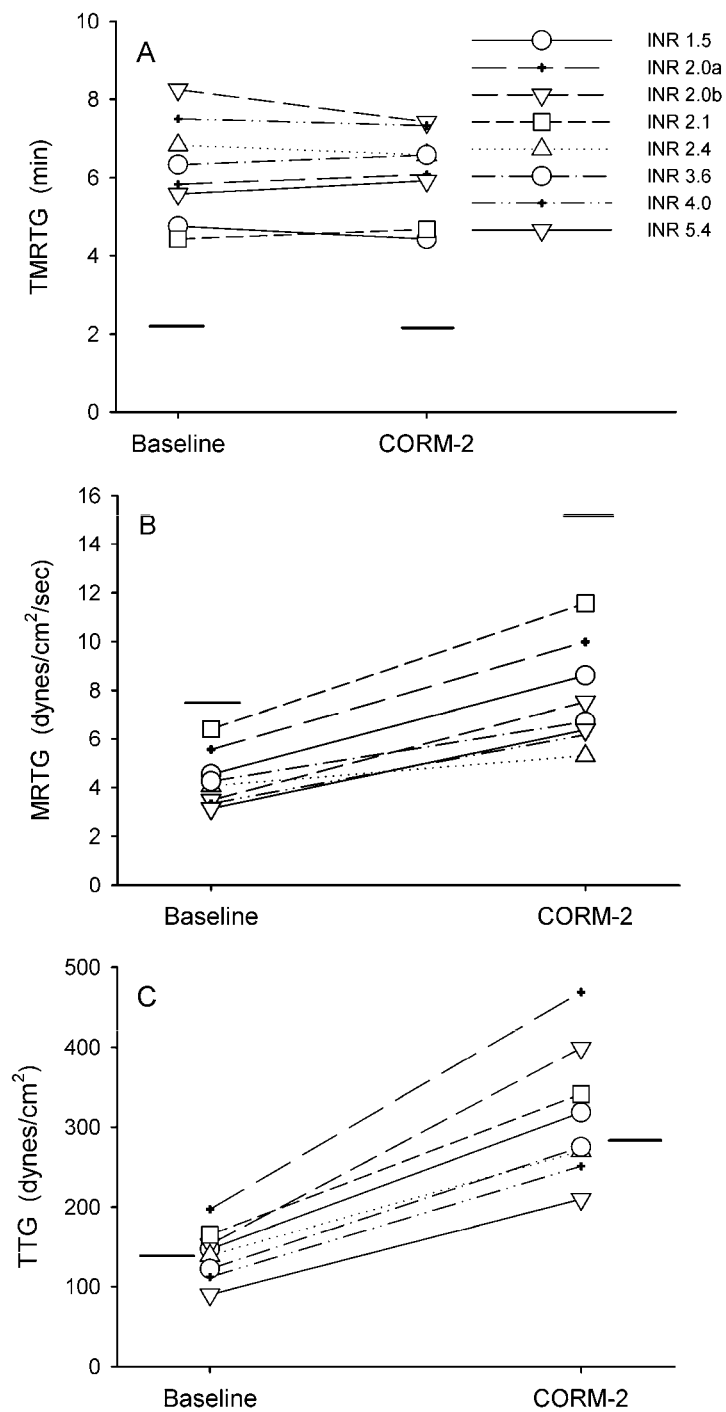
FIG. 20 is a graph showing the effect of CORM-2 on thrombus formation with 100 U/mL tissue-type plasminogen activator (tPA) present. Baseline=0 μM CORM-2; CORM-2=100 μM CORM-2. Individual subjects are identified according to the legend in panel A. The short horizontal bars represent the mean value derived from normal human plasma with INR=1.0.

As noted in FIG. 20, panel A, TMRTG values varied by −10% to 6% of baseline values following CORM-2 exposure, with values of all warfarin-treated subjects exceeding normal plasma mean values. As displayed in panel B, all subjects (including the one with INR 1.5) had an increase in MRTG values of 30% to 116% of baseline values in response to CORM-2 exposure. However, in all cases, subject plasma values for MRTG were less than that observed with normal plasma. With regard to clot strength, as seen in panel B, all subjects had an increase of 94% to 161% of baseline values in response to CORM-2 addition. Last, 4 of 8 subjects (INR 1.5, 2.0, 2.1) had an increase in clot strength after CORM-2 exposure that exceeded the mean value of normal plasma.

Figure 21:
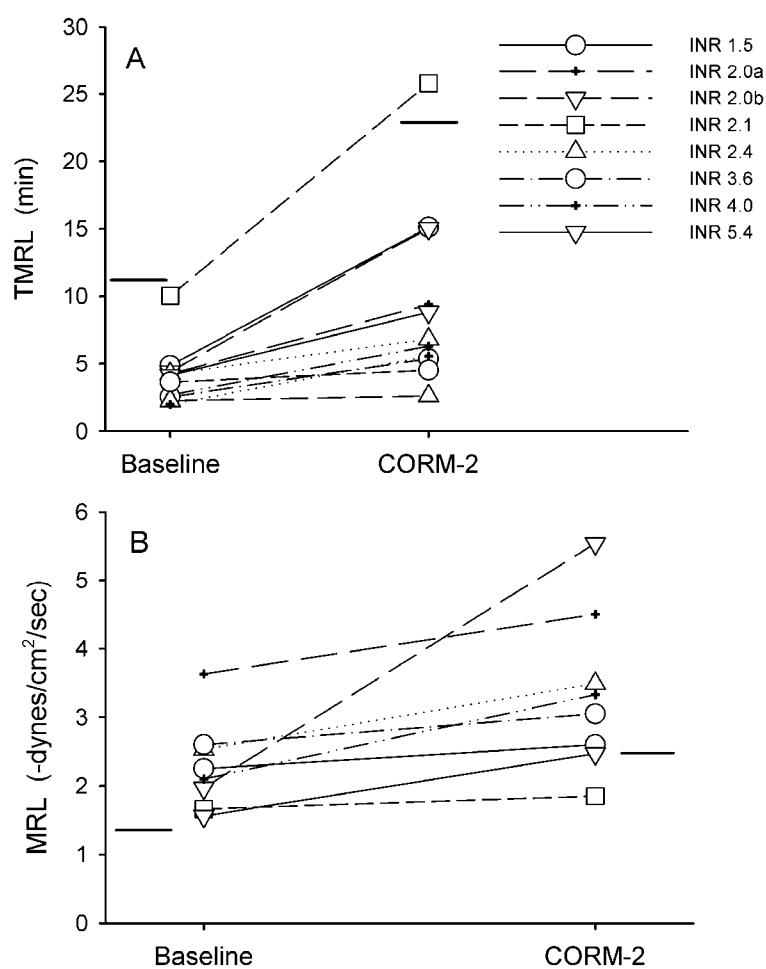
FIG. 21 is a graph showing the effect of CORM-2 on fibrinolysis. Baseline=0 μM CORM-2; CORM-2=100 μM CORM-2. Individual subjects are identified according to the legend in panel A. The short horizontal bars represent the mean value derived from normal human plasma with INR=1.0.

With regard to CORM-2 mediated changes in fibrinolysis, as seen in FIG. 21, panel A, all subjects had a delay in the onset of maximum rate of fibrinolysis, with values increasing 60% to 242% compared to baseline. However, all but one subject (INR 2.1) had TMRL values well below those of normal plasma, indicative of enhanced fibrinolysis. Similarly, as displayed in panel B, MRL was enhanced in all subjects with values increased by 11-181% of baseline values. In general, MRL values of subject plasma were greater than normal plasma.

Figure 22:
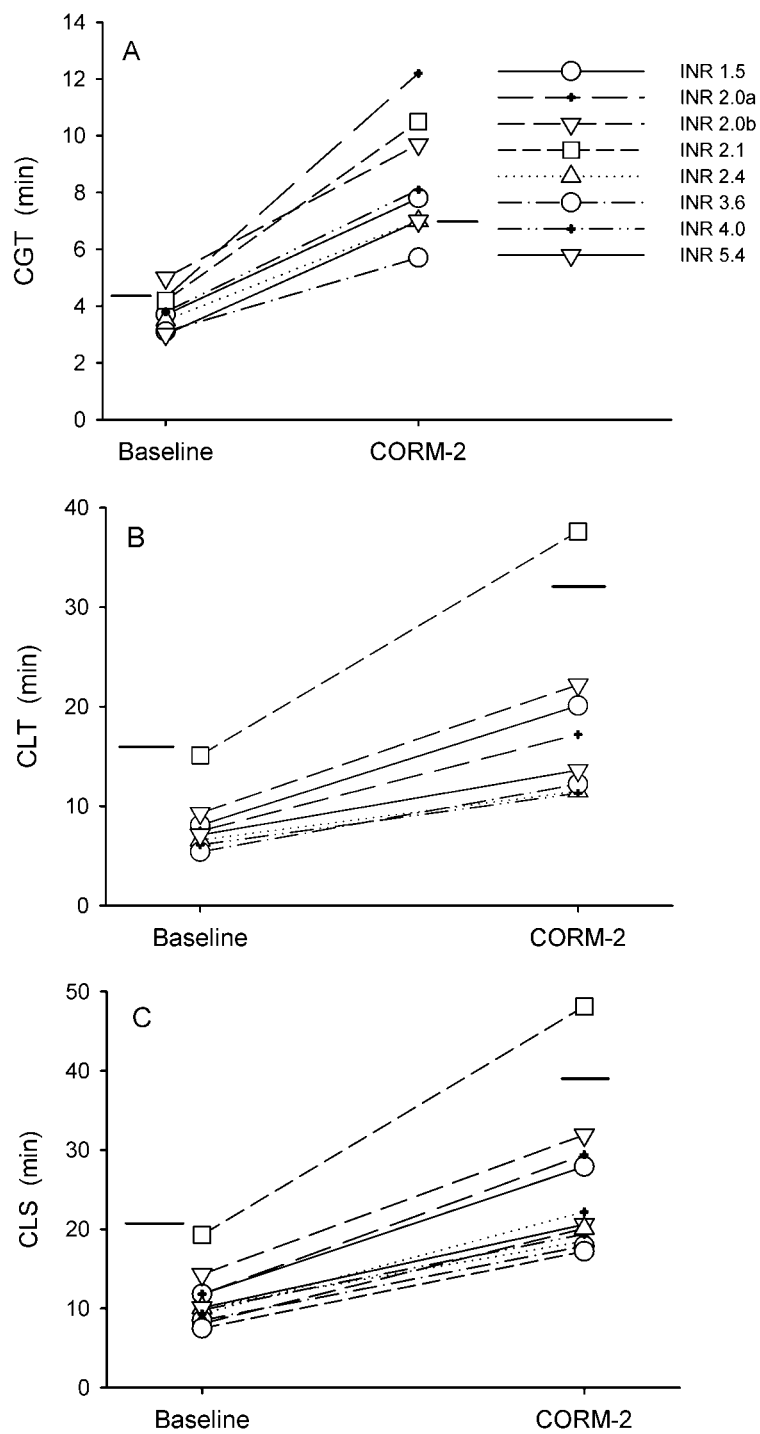
FIG. 22 is a graph showing the effect of CORM-2 on clot lifespan. Baseline=0 μM CORM-2; CORM-2=100 μM CORM-2. Individual subjects are identified according to the legend in panel A. The short horizontal bars represent the mean value derived from normal human plasma with INR=1.0.

As for clot lifespan parameters, as seen in FIG. 22, panel A, clot growth time was prolonged 84% to 184% of baseline values following CORM-2 addition. Five of eight subjects (INR 1.5, 2.0, 2.1, 4.0, 5.4) had an above normal increase in CGT in response to CORM-2. With regard to clot lysis time, CORM-2 exposure increased subject plasma values by 74% to 149% of baseline; however, only one subject (INR 2.1) had a response to CORM-2 that exceeded the mean value of normal plasma. The clot lifespan was increased in all subjects with CORM-2 exposure as displayed in panel C. All but one subject (INR 2.1) had a CLS value greater than that seen with normal plasma.

TABLE 7

Thrombelastographic Values in Normal Plasma Following CORM-2 Exposure.

| | 0 μM CORM-2 | 100 μM CORM-2 | Percent Change |
|---|---|---|---|
| | No tPA | | |
| TMRTG | 2.38 ± 0.05 | 2.26 ± 0.03* | −5% |
| MRTG | 7.4 ± 0.5 | 15.0 ± 2.4* | 102% |
| TTG | 168 ± 6 | 285 ± 38* | 70% |
| | tPA (100 U/ml) | | |
| TMRTG | 2.20 ± 0.07 | 2.14 ± 0.05 | −2% |
| MRTG | 7.7 ± 0.6 | 15.2 ± 1.3* | 97% |
| TTG | 138 ± 5 | 284 ± 27* | 106% |
| TMRL | 11.27 ± 2.10 | 22.92 ± 1.93* | 103% |
| MRL | −1.4 ± 0.3 | −2.4 ± 0.5* | 68% |
| CGT | 4.42 ± 1.05 | 7.00 ± 0.94* | 58% |
| CLT | 16.02 ± 2.46 | 32.07 ± 3.15* | 100% |
| CLS | 20.43 ± 2.73 | 39.07 ± 2.82* | 91% |

Data are presented as mean ± SD. tPA = tissue type plasminogen activator; TMRTG = time to maximum rate of thrombus generation (min); MRTG = maximum rate of thrombus generation (dynes/cm$^2$/sec); TTG = total thrombus generation (dynes/cm$^2$); TMRL = time to maximum rate of lysis (min); MRL = maximum rate of lysis (−dynes/cm$^2$/sec); CGT = clot growth time (min); CLT = clot lysis time (min); CLS = clot lifespan (min).
*P < 0.005 vs. 0 μM CORM-2.

Discussion

CORM-2 exposure enhanced coagulation and diminished fibrinolytic vulnerability in plasma obtained from subjects chronically anticoagulated with warfarin. With regard to coagulation in samples obtained from these subjects, CORM-2 exposure had the greatest effect on clot strength and growth time, with positive but lesser effects on speed of clot growth, onset of lysis and clot lysis time. The rate of lysis was increased in normal plasma by CORM-2 as described in Example 2, suggesting that when antifibrinolytic defenses are finally breached that the three dimensional relationships of fibrin polymers favors plasmin-mediated disintegration. However, in normal and anticoagulated subject plasma, the CORM-2 mediated increase in clot strength and prolongation of onset of fibrinolysis via improved efficiency of antifibrinolytic enzymes (e.g., plasminogen activator inhibitor 1) appeared to offset the effects of increased MRL as shown in Example 2. The TMRL and CLT values of warfarin-treated subjects were relatively smaller than the normal plasma values. CORM-2 exposure improved coagulation and attenuated fibrinolysis in plasma obtained from warfarin-treated subjects, but these effects were generally of less magnitude that that observed in normal plasma.

Example 7

Effects of Carbon Monoxide Releasing Agents on Fibrinogen-Dependent Coagulation Kinetics and Prothrombin Activity Materials and Methods Plasma types, purified proteins and compounds. Prothrombin deficient plasma (George King Bio-Medical, Overland Park, Kans.) anticoagulated with sodium citrate was utilized for experimentation concerning the effects of CORM-2 on prothrombin. Purified prothrombin (Enzyme Research Laboratories, South Bend, Ind.) that was 95% pure (10.4 mg/mL, 11.1 U/mg, suspended in 20 mM Tris-HCl in 0.1M NaCl at pH 7.4) was used for experimentation. Fibrinogen deficient plasma (Affinity Biologicals, Inc., Ancaster, Ontario, Canada) anticoagulated with sodium citrate was used in experiments investigating the effects of CORM-2 on fibrinogen. This plasma had a fibrinogen concentration of 15 mg/dL, a prothrombin activity of 0.91 U/mL, a prothrombin time of >120 sec, and an activated partial thromboplastin time of >180 sec. Purified fibrinogen (Enzyme Research Laboratories) that was >95% clottable at a concentration of 43.5 mg/mL (dissolved in 20 mM sodium citrate-HCl at pH 7.4) was utilized in experiments with fibrinogen deficient plasma. CORM-2 and dimethyl sulfoxide (DMSO) were obtained from Sigma-Aldrich, St. Louis, Mo.

Exposure of purified prothrombin to CORM-2. In order to determine if pre-exposure of prothrombin with CORM-2 would enhance coagulation kinetics in prothrombin deficient plasma, 396 µL of pure prothrombin solution was combined with 4 µL of either DMSO or CORM-2 in DMSO for a final concentration of 0 or 100 µM CORM-2. This solution was incubated for 5 min at 37° C. prior to being added to prothrombin deficient plasma for thrombelastographic analyses. A volume of 3.1 µL of incubated solution was added to the final reaction mixture subsequently presented for a final prothrombin activity of 1 U/mL. The final concentration of CORM-2 in the plasma sample mixture was <10 µM, a concentration which does not affect coagulation kinetic values in this system (Examples 1 and 2).

Exposure of purified fibrinogen to CORM-2. Experiments with purified fibrinogen pre-exposure to CORM-2 were to be performed in a similar fashion as that described with prothrombin. However, CORM-2 in DMSO was not soluble in either pure fibrinogen solution or in up to three-fold diluted fibrinogen solution. The added CORM-2 formed a white-yellow precipitate under these conditions. Therefore, a concentration-response relationship between various fibrinogen concentrations with or without the addition of CORM-2 was generated as outlined subsequently.

Prothrombin deficient plasma experiments. The final volume for experiments involving prothrombin deficient plasma was 359.1-360.7 µL. In experiments involving pre-exposure of prothrombin to 0 or 100 µM CORM-2 (n=7 per concentration), the sample consisted of 326 µL of prothrombin deficient plasma, 3.1 µL of prothrombin solution, 10 µL of tissue factor reagent (0.1% final concentration in dH$_2$O; Instrumentation Laboratory, Lexington, Mass.), and 20 µL of 200 mM CaCl$_2$. In experiments involving simple CORM-2 addition (positive control) to the reactants, the sample mixture consisted of 324 µL of prothrombin deficient plasma, 3.1 µL of prothrombin solution, 3.6 µL of DMSO or CORM-2 in DMSO (final CORM-2 concentration 0 or 100 µM, n=8 per concentration), 10 µL of tissue factor reagent (0.1% final concentration), and 20 µl of 200 mM CaCl$_2$.

Fibrinogen deficient plasma experiments. In these experiments, the final plasma sample mixture volume was 358.6 µL. Sample composition consisted of 260 µL of fibrinogen deficient plasma, 65 µL of pure fibrinogen solution, and dH$_2$O to generate discrete fibrinogen concentrations subsequently described, 3.6 µL of DMSO or CORM-2 in DMSO (final CORM-2 concentration 0 or 100 µM, n=4 per fibrinogen concentration), 10 µL of tissue factor reagent (0.1% final concentration), and 20 µL of 200 mM CaCl$_2$. The fibrinogen concentrations studied were 100, 200, 300, 400, 500, 600, and 800 mg/dL.

Thrombelastographic monitoring. Plasma sample mixtures were placed in a disposable cup in a computer-controlled THROMBELASTOGRAPH® hemostasis system (Model 5000, Haemoscope Corp., Niles, Ill.), with addition of CaCl$_2$ as the last step to initiate clotting. Data were collected until clot strength stabilized. The following previously described variables (Examples 1-3) were determined at 37° C.: Time to maximum rate of thrombus generation (TMRTG): This is the time interval (sec) observed prior to maximum speed of clot growth. Maximum rate of thrombus generation (MRTG): This is the maximum velocity of clot growth observed (dynes/cm$^2$/sec). Total Thrombus Generation (TTG): This is the total area under the velocity curve during clot growth (dynes/cm$^2$), representing the amount of clot strength generated during clot growth.

Statistical Analyses. Data obtained from experiments involving prothrombin deficient plasma are presented as mean±SD. Typically, n=6-8 provides statistical power >0.8 in similar analyses (Examples 1 and 2). Analyses of the effects of CORM-2 on thrombelastographic variables were conducted using unpaired, two-tailed Student's t-tests. A P value of <0.05 was considered significant. Graphical representation of the thrombelastographic data derived from experiments with fibrinogen deficient plasma was generated with commercially available software (SigmaPlot 11.0, Systat Software, Inc., San Jose, Calif.). Coagulation kinetic model equations were derived with the same software. The difference between the mean values of MRTG or TTG in samples exposed to 0 or 100 µM CORM-2 were determined and expressed as percent difference secondary to CORM-2 exposure in the fibrinogen deficient plasma experiments. These data are depicted graphically with Origin 7.5, OriginLab Corp., Northampton, Mass.

Results

Prothrombin deficient plasma experiments. As shown in Table 8, pretreatment of purified prothrombin with CORM-2 did not significantly change coagulation kinetics in prothrombin deficient plasma as compared to prothrombin exposed to DMSO vehicle alone. In contrast, addition of CORM-2 to prothrombin deficient plasma mixed with purified prothrombin resulted in marked enhancement of MRTG and TTG values compared to addition of vehicle alone.

Figure 23:
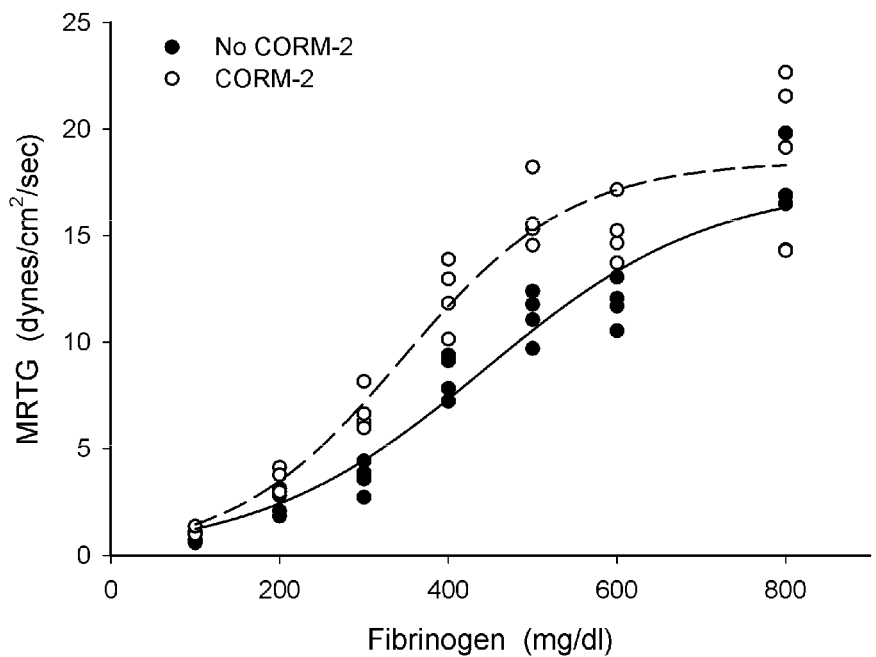
FIG. 23 is a graph showing the MRTG response to increasing fibrinogen concentration in the presence of 0 or 100 μM CORM-2. Increases in fibrinogen concentration enhanced MRTG values in samples exposed to 0M CORM-2 (black circles). A similar, but enhanced correlation of MRTG values with fibrinogen concentration was observed following exposure to 100 μM CORM-2 (hollow circles). The solid line represents the sigmoidal curve fit for samples exposed to 0 μM CORM-2, whereas the dashed line represents the sigmoidal curve fit for plasma exposed to 100 μM CORM-2.
Figure 24:
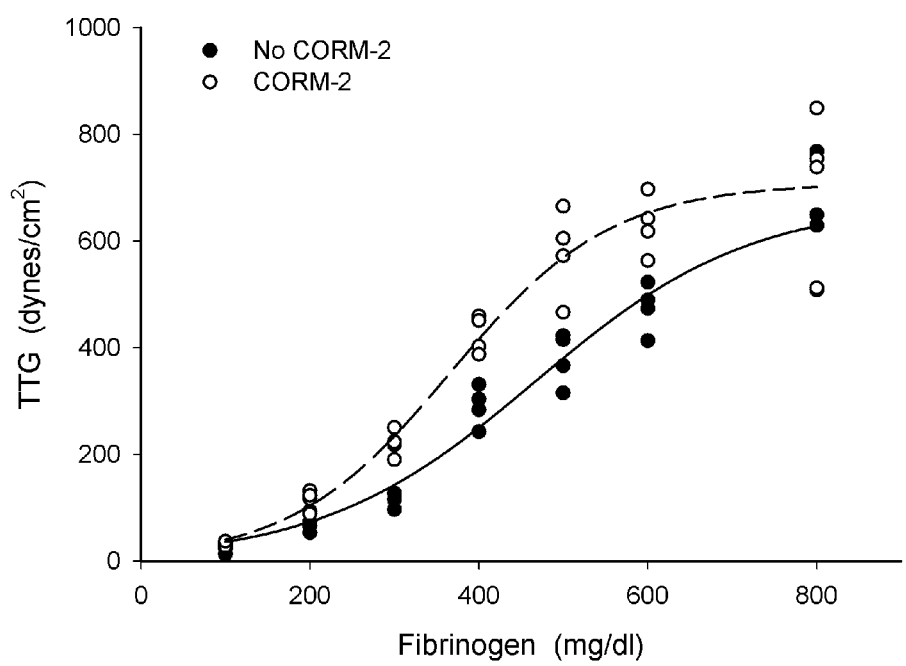
FIG. 24 is a graph showing the TTG response to increasing fibrinogen concentration in the presence of 0 or 100 μM CORM-2. Increases in fibrinogen concentration enhanced TTG values in samples exposed to 0 μM CORM-2 (black circles). A similar, but enhanced correlation of TTG values with fibrinogen concentration was observed following exposure to 100 μM CORM-2 (hollow circles). The solid line represents the sigmoidal curve fit for samples exposed to 0 μM CORM-2, whereas the dashed line represents the sigmoidal curve fit for plasma exposed to 100 μM CORM-2.

Fibrinogen deficient plasma experiments. As depicted in FIGS. 23 and 24, the generation of progressively greater fibrinogen concentrations in fibrinogen deficient plasma resulted in a sigmoidal increase in MRTG and TTG values. The addition of CORM-2 resulted in a different sigmoidal response of MRTG and TTG to increasing fibrinogen concentrations. While MRTG and TTG values were similar between samples exposed to 0 or 100 µM CORM-2 at the extremes of the range of fibrinogen concentration tested (e.g., 100 and 800 mg/dL), there was a separation between the two conditions within the mid-range of fibrinogen concentration values. With regard to TMRTG, there was no noticeable difference between samples exposed to 0 or 100 µM CORM-2 throughout the range of fibrinogen concentrations tested. There was a linear correlation with increasing fibrinogen concentrations with an increase of TMRTG values noted; in samples exposed to 0 µM CORM-2 the range of values was 2.83-4.75 min, whereas samples exposed to 100 µM CORM-2 the range of values was 2.83-4.00 min. Table 9 displays the individual fitting equations, coefficients of determination and statistical significance of the aforementioned correlations.

Figure 25:
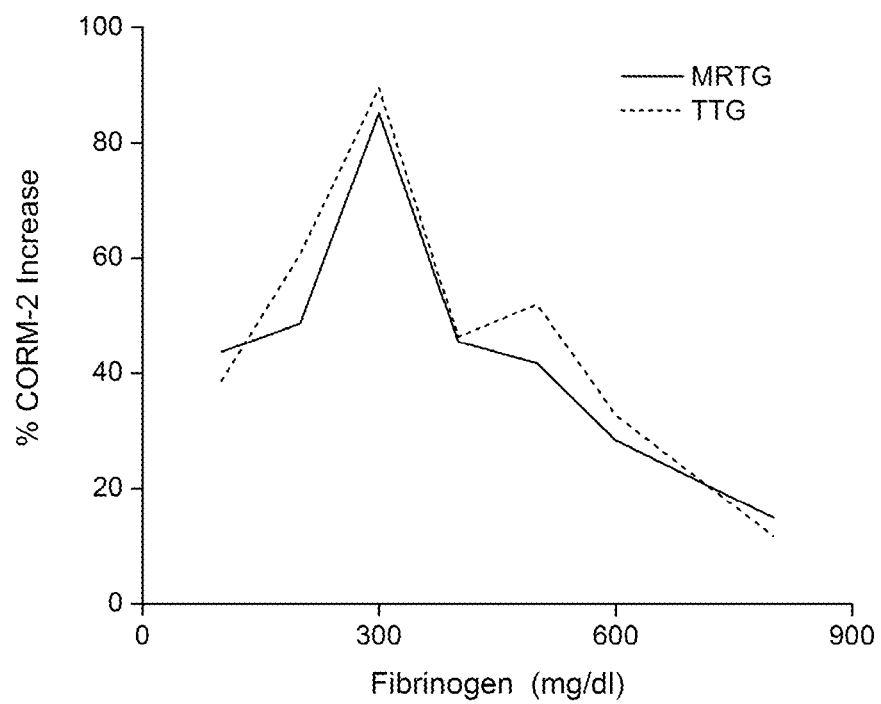
FIG. 25 is a graph showing CORM-2 mediated enhancement of MRTG and TTG. Exposure of plasma with progressively greater fibrinogen concentration to 100 μM CORM-2 resulted in a "bell-shaped" enhancement of MRTG and TTG. Percent (%) CORM-2 Increase=the percentage difference between the means of samples exposed to 0 or 100 μM CORM-2 at the indicated fibrinogen concentrations.

FIG. 25 displays the relative increase in MRTG and TTG values over the range of fibrinogen concentration utilized. The CORM-2 mediated enhancement of MRTG and TTG kinetics was "bell-shaped", with an approximate 30% to >80% increase in both parameters noted within the normal range of fibrinogen concentration. MRTG and TTG were optimized at a fibrinogen concentration of 300 mg/dL, with a >80% increase in both parameters secondary to CORM-2 exposure.

TABLE 8

Thrombelastographic Coagulation Values in Prothrombin Deficient Plasma

|  | 0 µM CORM-2 | 100 µM CORM-2 |
|---|---|---|
| CORM-2 Pre-exposure Experiments | | |
| TMRTG | 1.83 ± 0.00 | 2.15 ± 0.56 |
| MRTG | 4.96 ± 0.28 | 4.65 ± 0.99 |
| TTG | 86 ± 4 | 88 ± 3 |
| CORM-2 Addition Experiments | | |
| TMRTG | 1.87 ± 0.07 | 1.85 ± 0.04 |
| MRTG | 5.74 ± 0.35 | 9.17 ± 0.36* |
| TTG | 97 ± 4 | 152 ± 7* |

Data is presented as mean ± SD. TMRTG = time to maximum rate of thrombus generation (min); MRTG = maximum rate of thrombus generation (dynes/cm$^2$/sec); TTG = total thrombus generation (dynes/cm$^2$).
*P < 0.05 vs. 0 µM CORM-2.

TABLE 9

Curve Fitting Equations Describing the Correlation of Thrombelastographic Parameters with Fibrinogen Concentrations without or with CORM-2 Exposure.

| Parameter | Equation | $R^2$ | P Value |
|---|---|---|---|
| 0 µM CORM-2 | | | |
| TMRTG | TMRTG = 2.84 + (0.00161 X [fibrinogen])* | 0.71 | <0.001 |
| MRTG | MRTG = −19.8/(1 + e$^{(-([fibrinogen]+423)/-83.5)}$)** | 0.94 | <0.0001 |
| TTG | TTG = −768/(1 + e$^{(-([fibrinogen]+456)/-73.0)}$)** | 0.94 | <0.0001 |
| 100 µM CORM-2 | | | |
| TMRTG | TMRTG = 2.95 + (0.00098 X [fibrinogen])* | 0.52 | <0.001 |
| MRTG | MRTG = −22.7/(1 + e$^{(-[fibrinogen]+364)/-65.2)}$)** | 0.92 | <0.0001 |
| TTG | TTG = −849/(1 + e$^{(([fibrinogen]+376)/-58.5)}$)** | 0.94 | <0.0001 |

*Equation Category: Linear Regression;
**Equation Category: Sigmoidal; TMRTG = time to maximum rate of thrombus generation (min); MRTG = maximum rate of thrombus generation (dynes/cm$^2$/sec); TTG = total thrombus generation (dynes/cm$^2$); [fibrinogen] = fibrinogen concentration in mg/dL.

Discussion

CORM-2 pre-exposure did not enhance prothrombin mediated coagulation kinetics in plasma; instead, only addition of CORM-2 to prothrombin deficient plasma mixed with prothrombin resulted in enhanced MRTG and TTG values. In addition, CORM-2 modifies fibrinogen as a substrate for thrombin. Specifically, the "bell-shaped" relationship of CORM-2 enhanced MRTG and TTG with fibrinogen concentration strongly supports the notion that CORM-2 is enhancing fibrinogen as a substrate in this plasma system. Expressed in another way, the effects of CORM-2 on fibrinogen require a minimum concentration of fibrinogen to have observable effects, whereas CORM-2 mediated effects at a fixed concentration are subsequently overshadowed by large concentrations of fibrinogen (with bound factor XIII). Thus, whatever effect CORM-2 is having on fibrinogen at a concentration of 800 mg/dL, that effect is hidden in the much greater effect of factor XIII-mediated fibrin polymer crosslinking which is kinetically competing with CORM-2 effects on fibrinogen.

Example 8

Effects of Carbon Monoxide Releasing Agents on Coagulation and Fibrinolysis in Diluted Plasma Materials and Methods Plasma and volume expanders. Pooled normal plasma (George King Bio-Medical, Overland Park, Kans.) anticoagulated with sodium citrate was utilized for experimentation. The lot of plasma had a prothrombin time of 12.8 seconds, international normalized ratio value of 1.0, an activated partial thromboplastin time of 29.4 seconds, and a fibrinogen concentration of 310 mg/dL. The volume expanders tested were 0.9% NaCl (Abbott Laboratories, North Chicago, Ill.; also designated as NS) and 6% hydroxylethyl starch (HES) in 0.9% NaCl (VOLUVEN®, average molecular weight 130 kDa, 0.4 degree of substitution, C2:C6 ratio of substitution 11.2; Fresenius Kabi, Bad Homburg, Germany; also referred to as VOL).

Plasma sample composition of dilution-response experiments. The final volume for all subsequently described plasma sample mixtures was 359.6 µL. Sample composition consisted of 326 µL of plasma/volume expander, 10 µL of tissue factor reagent (0.1% final concentration in dH$_2$O; Instrumentation Laboratory, Lexington, Mass.), 3.6 µL of dimethyl sulfoxide (DMSO) or DMSO with CORM-2 (100

μM final concentration; Sigma-Aldrich, St. Louis, Mo.), and 20 μL of 200 mM CaCl$_2$. Tissue factor stock was kept on ice prior to use and was remade every two hours. The concentration of CORM-2 used was that associated with maximal effect on coagulation and fibrinolysis in this system (see Example 2). DMSO was added to dry CORM-2 just prior to placement into the plasma mixture. Plasma was diluted 0%, 20%, 30%, 40% or 50% with NS or VOL (n=4 per condition).

Plasma sample composition of experiments with tissue-type plasminogen activator addition. As in the first series of experiments, the final volume of plasma sample mixtures was 359.6 μL. Sample composition consisted of 316 μL of plasma/volume expander, 10 μL of tissue factor reagent (0.1% final concentration), 3.6 μL of DMSO without or with CORM-2 (100 μM final concentration), 10 μL of tissue-type plasminogen activator (tPA, 580 U/μg, Genentech, Inc., San Francisco, Calif.) diluted with 10 mM potassium phosphate buffer (pH 7.4) for a final activity of 100 IU/mL, and 20 μL of 200 mM CaCl$_2$. As with tissue factor reagent, tPA stock was kept on ice prior to use and was remade every two hours. Plasma was diluted 0% or 30% with NS or VOL (n=8 per condition).

Clot Lifespan Model (CLSM) Analyses. Plasma sample mixtures were placed in a disposable cup in a computer-controlled THROMBELASTOGRAPH® hemostasis system (Model 5000, Haemoscope Corp., Niles, Ill.), with addition of CaCl$_2$ as the last step to initiate clotting. In the first series of experiments, no tPA was added, so data were collected until clot strength (maximum amplitude) was stable. In the second series of experiments which in tPA was added, data were collected until clot lysis time occurred. The following variables were determined at 37° C. depending on whether or not tPA was present in the reaction mixture: clot growth time (CGT, time from clot amplitude of 2 mm [102 dynes/cm$^2$] until maximum strength is achieved, in sec), clot lysis time (CLT, time from when maximum strength was observed to 2 mm amplitude, in sec), and clot lifespan (CLS, the sum of CGT and CLT). Additional elastic modulus-based parameters were determined and the nomenclature used to describe these phenomena is as follows: Time to maximum rate of thrombus generation (TMRTG): This is the time interval (sec) observed prior to maximum speed of clot growth. Maximum rate of thrombus generation (MRTG): This is the maximum velocity of clot growth observed (dynes/cm$^2$/sec). Total Thrombus Generation (TTG): This is the total area under the velocity curve during clot growth (dynes/cm$^2$), representing the amount of clot strength generated during clot growth. Time to maximum rate of lysis (TMRL): This is the time interval (sec) measured from the time of maximum strength to the time when the velocity of clot disintegration is maximal. Maximum Rate of Lysis (MRL): This is the maximum velocity of clot disintegration observed (−dynes/cm$^2$/sec). Area of Clot Lysis (ACL): This is the total area under the velocity curve during clot disintegration (−dynes/cm$^2$), representing the amount of clot strength lost during clot disintegration. As this model involves complete fibrinolysis, TTG is equivalent to ACL, so ACL was not presented as it provides no additional information.

Statistical Analyses. Data obtained from pooled normal plasma not exposed to tPA were graphically represented with commercially available software (SigmaPlot 11.0, Systat Software, Inc., San Jose, Calif.), and kinetic modeling of thrombelastographic data performed with the same software. Analyses of the effects of hemodilution and CORM-2 on CLSM variables obtained from pooled normal plasma were conducted using Kruskal-Wallis one way analysis of variance with Student-Newman-Keuls post-hoc test. These data were represented as median and 1$^{st}$-3$^{rd}$ quartiles. These analyses were conducted with the same commercially available software (SigmaPlot 11.0). A P value of <0.05 was considered significant.

Results

Dilution-response experiments. Data from these experiments are displayed in FIGS. 26 and 27, with the derived kinetic equations and coefficients of determination depicted in Table 10. With regard to TMRTG, there was a significant tendency to decrease in value with progressive dilution regardless of condition, with a range of 2.8 to 1.9 min in the samples exposed to NS and a range of 2.8 to 2.0 min in the samples exposed to VOL.

Figure 26:
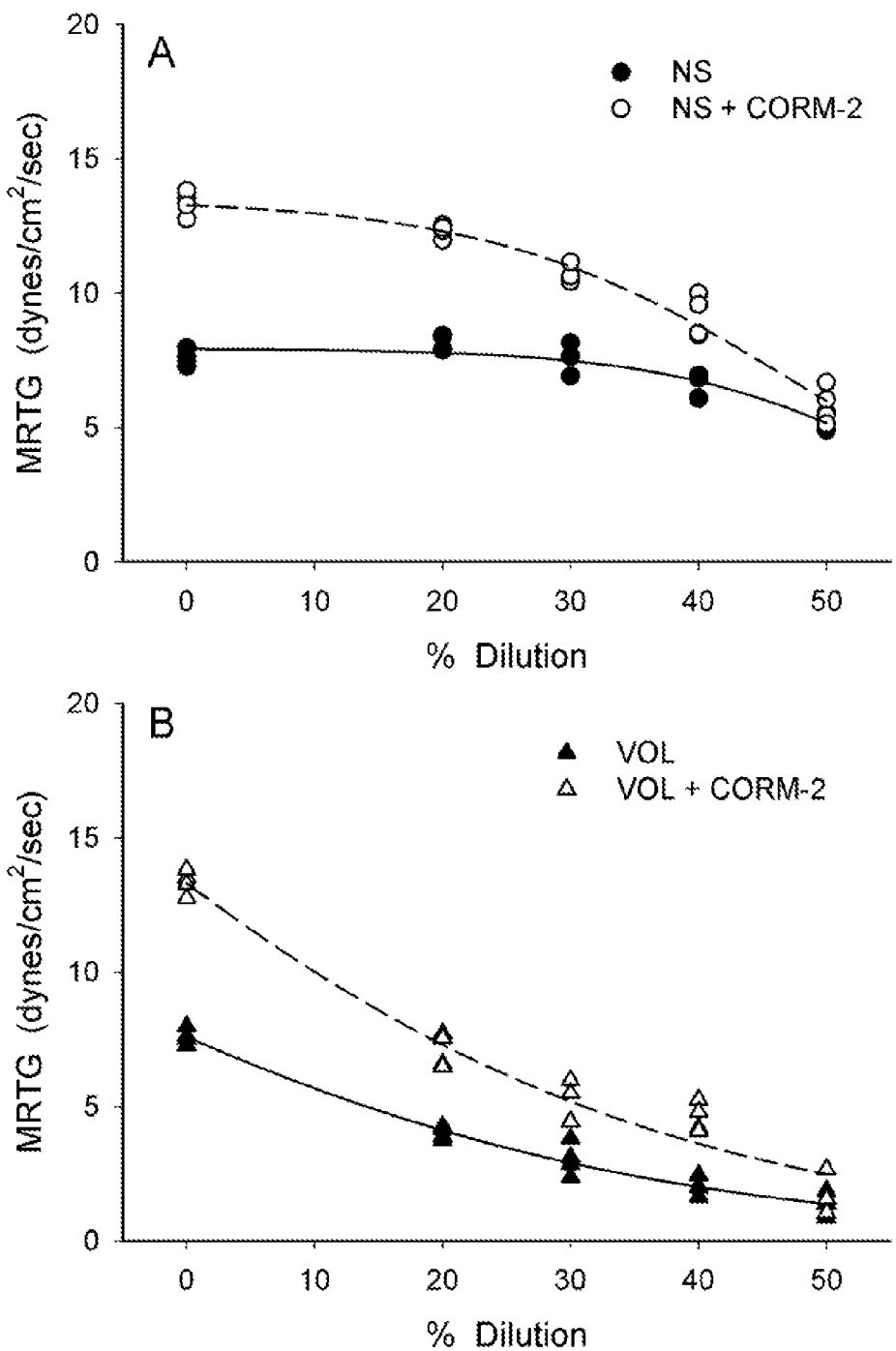
FIG. 26 is a graph showing the MRTG response to increasing the degree of dilution of plasma with sodium chloride (NS) or low molecular weight hydroxyethyl starch (VOL) in the presence of 0 or 100 μM CORM-2. Panel A displays the dilution results with sodium chloride and Panel B displays the dilution results with low molecular weight hydroxyethyl starch. The solid line represents the curve fit for samples exposed to 0 μM CORM-2, whereas the dashed line represents the curve fit for plasma exposed to 100 μM CORM-2.

In contrast to TMRTG, as seen in FIG. 26, exposure to CORM-2 increased MRTG by 75% in undiluted samples. As depicted in panel A of FIG. 26, MRTG values did not decrease before plasma samples were diluted 40% and 50% with NS (14% and 32% decrease compared with undiluted samples). Samples diluted with NS and exposed to CORM-2 had MRTG values 40-50% greater than matched diluted samples not exposed to CORM-2, with the exception of samples diluted 50% that had MRTG values increased by only 12% with CORM-2 exposure. CORM-2 exposure resulted in supranormal MRTG values in samples diluted with NS with the exception of samples diluted 50%. In contrast to samples diluted with NS, plasma diluted with VOL demonstrated an immediately progressive decrease in MRTG values as displayed in FIG. 26, panel B. Twenty percent, 30%, 40% and 50% dilution with VOL resulted in MRTG values of 52%, 39%, 26%, and 17% of undiluted sample values, respectively. Exposure of VOL-diluted plasma to CORM-2 improved MRTG values, with 20%, 30%, 40%, and 50% dilution resulting in MRTG values 93%, 67%, 60%, and 22% of undiluted samples, respectively. In sum, CORM-2 exposure resulted in supranormal MRTG values in plasma diluted with NS, but could only partially compensate for VOL-mediated decreases in MRTG values.

Figure 27:
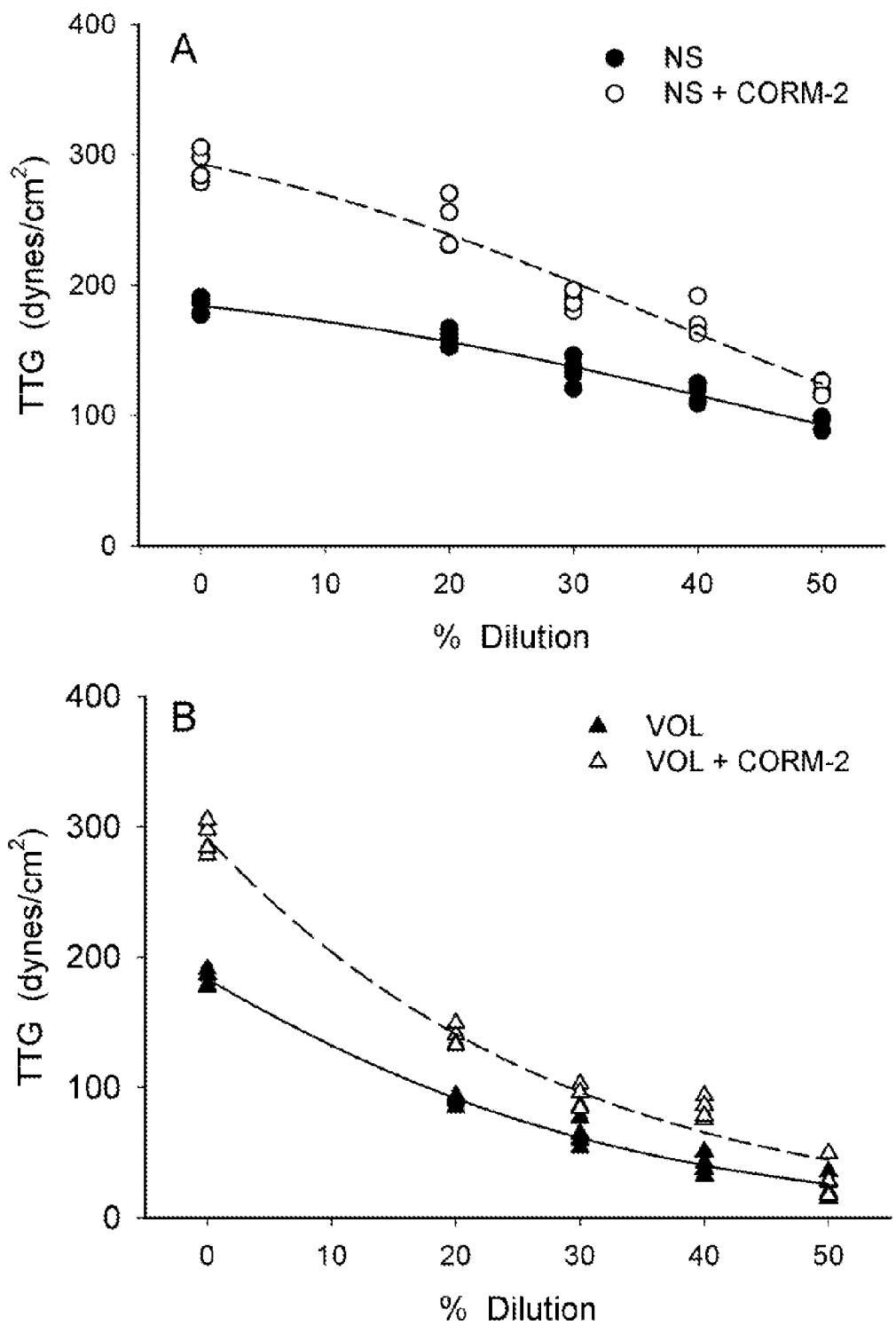
FIG. 27 is a graph showing the TTG response to increasing the degree of dilution of plasma with sodium chloride (NS) or low molecular weight hydroxyethyl starch (VOL) in the presence of 0 or 100 μM CORM-2. Panel A displays the dilution results with sodium chloride and Panel B displays the dilution results with low molecular weight hydroxyethyl starch. The solid line represents the curve fit for samples exposed to 0 μM CORM-2, whereas the dashed line represents the curve fit for plasma exposed to 100 μM CORM-2.

Similar to MRTG, as seen in FIG. 27, exposure to CORM-2 increased TTG by 59% in undiluted samples. As depicted in panel A of FIG. 27, dilution of plasma with NS by 20%, 30%, 40% and 50% resulted in TTG values 87%, 73%, 63% and 50% of undiluted sample values. CORM-2 exposure increased TTG values of NS-diluted samples between 31%-54%, with supranormal clot strength observed until plasma was 40% diluted. In contrast to samples diluted with NS, plasma diluted with VOL demonstrated a more progressive decrease in TTG values as displayed in FIG. 27, panel B. Twenty percent, 30%, 40%, and 50% dilution with VOL resulted in TTG values of 49%, 35%, 22%, and 13% of undiluted sample values, respectively. Exposure of VOL-diluted plasma to CORM-2 improved TTG values, with 20%, 30%, 40%, and 50% dilution resulting in TTG values 76%, 50%, 45%, and 17% of undiluted samples, respectively. In sum, CORM-2 exposure resulted in supranormal TTG values in plasma diluted with NS, but could only marginally compensate for VOL-mediated decreases in TTG values.

Experiments with tPA addition. Comparisons of the effects of CORM-2 exposure in undiluted and diluted plasma following fibrinolytic stress are displayed in Table 11. CORM-2 exposure resulted in faster growing, stronger clots that took longer to form and dissolve under all conditions. Nevertheless, VOL diluted plasma formed the slowest growing, weakest clots that took the least time to form and fibrinolysed most rapidly. Specifically, VOL diluted plasma thrombi lasted approximately one third as long as undiluted plasma, with only 31% of the MRTG and 25% of the TTG values of undiluted plasma. While CORM-2 exposure enhanced VOL-diluted plasma CLSM values, these values were still less than that observed in undiluted or NS-diluted samples. With regard to fibrinolytic kinetics, NS-diluted samples had less increase in MRL and greater CLT/CLS values following CORM-2 exposure compared to undiluted samples.

TABLE 10

Correlation Equations of Thrombelastographic Parameters and % Dilution without or with CORM-2 Exposure.

| Parameter | Equation | $R^2$ | P Value |
|---|---|---|---|
| | 0.9% NaCl; Without CORM-2 | | |
| TMRTG | TMRTG = 2.46 + (0.00977 X %dilution)* | 0.63 | <0.001 |
| MRTG | MRTG = 7.94/(1 + $e^{(-(\%dilution-55.7)/-9.20)}$)** | 0.85 | <0.0001 |
| TTG | TTG = 211/(1 + $e^{(-(\%dilution-44.3)/-23.1)}$)** | 0.96 | <0.0001 |
| | 0.9% NaCl; With CORM-2 | | |
| TMRTG | TMRTG = 2.35 + (0.00517 X %dilution)* | 0.33 | <0.01 |
| MRTG | MRTG = 13.51/(1 + $e^{(-(\%dilution-47.3)/-11.8)}$)** | 0.96 | <0.0001 |
| TTG | TTG + 344/(1 + $e^{(-(\%dilution-37.7/-21.5)}$)** | 0.95 | <0.0001 |
| | 6% Hydroxyethyl Starch; Without CORM-2 | | |
| TMRTG | TMRTG = 2.51 + (0.00716 X %dilution)* | 0.59 | <0.001 |
| MRTG | MRTG = 22.3/(1 + $e^{(-(\%dilution+16.1)/-24.2)}$)** | 0.97 | <0.0001 |
| TTG | TTG = 517/1 + $e^{(-(\%dilution+12.8)/-21.4)}$)** | 0.98 | <0.0001 |
| | 6% Hydroxyethyl Starch; With CORM-2 | | |
| TMRTG | TMRTG = 2.39 + (0.00659 X %dilution)* | 0.52 | <0.001 |
| MRTG | MRTG = 38.5/(1 + $e^{(-(\%dilution+15.7)/-24.6)}$)** | 0.96 | <0.0001 |
| TTG | TTG = 2234/(1 + $e^{(-(\%dilution+47.4)/-25.0)}$)** | 0.97 | <0.0001 |

*Equation Category: Linear Regression;

**Equation Category: Sigmoidal; TMRTG = time to maximum rate of thrombus generation (min); MRTG = maximum rate of thrombus generation (dynes/cm$^2$/sec); TTG = total thrombus generation (dynes/cm$^2$).

TABLE 11

CLSM Values in Plasma with Following Dilution and CORM-2 Exposure.

| CORM-2 | − | + |
|---|---|---|
| | Undiluted | |
| TMRTG | 2.2 (2.2, 2.3) | 2.1 (2.1, 2.2)* |
| MRTG | 7.4 (6.9, 7.6) | 13.9 (13.5, 14.8)* |
| TTG | 145 (135, 152) | 285 (272, 290)* |
| TMRL | 7.7 (6.8, 8.6) | 17.7 (14.5, 21.5)* |
| MRL | −1.3 (−1.7, −1.2) | −3.0 (−3.3, −2.4)* |
| CGT | 3.5 (3.4, 3.8) | 8.1 (6.4, 8.6)* |
| CLT | 12.2 (11.9, 14.2) | 24.3 (19.6, 28.1)* |
| CLS | 15.8 (15.3, 17.6) | 31.6 (28.4, 35.2)* |
| | 30% NS | |
| TMRTG | 2.0 (2.0, 2.1)† | 2.00 (1.9, 2.0) |
| MRTG | 6.5 (5.9, 6.8)† | 11.2 (9.4, 11.4)*† |
| TTG | 105 (98, 112)† | 206 (192, 212)*† |
| TMRL | 9.6 (7.2, 10.3) | 23.4 (21.1, 26.9)*† |
| MRL | −1.6 (−1.7, −1.4) | −1.9 (−2.2, −1.5)† |
| CGT | 3.6 (3.5, 4.2) | 8.0 (7.2, 8.2)* |
| CLT | 11.6 (9.4, 12.4)† | 31.5 (28.7, 35.8)*† |
| CLS | 15.2 (14.4, 16.0) | 38.7 (36.7, 43.0)*† |
| | 30% VOL | |
| TMRTG | 2.1 (2.0, 2.1)† | 2.0 (2.0, 2.1) |
| MRTG | 2.3 (2.2, 2.5)†‡ | 3.8 (3.6, 4.1)*†‡ |
| TTG | 36 (34, 38)†‡ | 62 (58, 68)*†‡ |
| TMRL | 2.3 (2.0, 2.4)†‡ | 5.2 (4.9, 5.9)*†‡ |
| MRL | −0.9 (−1.3, −0.7)†‡ | −0.9 (−1.2, −0.8)†‡ |
| CGT | 1.6 (1.0, 1.9)†‡ | 2.2 (1.9, 2.4)*†‡ |

TABLE 11-continued

CLSM Values in Plasma with Following Dilution and CORM-2 Exposure.

| CORM-2 | − | + |
|---|---|---|
| CLT | 3.8 (3.1, 4.4)†‡ | 8.0 (7.4, 8.2)*†‡ |
| CLS | 5.2 (4.2, 6.4)†‡ | 10.0 (9.5, 10.4)*†‡ |

Data are presented as median(1$^{st}$, 3$^{rd}$ quartiles); NS = 0.9% NaCl; VOL = 6% hydroxyethyl starch; − = 0 μM CORM-2; + = 100 μM CORM-2' TMRTG = time to maximum rate of thrombus generation (min); MRTG = maximum rate of thrombus generation (dynes/cm$^2$/sec); TTG = total thrombus generation (dynes/cm$^2$); TMRL = time to maximum rate of lysis (min); MRL = maximum rate of lysis (−dynes/cm$^2$/sec); CGT = clot growth time (min); CLT = clot lysis time (min); CLS = clot lifespan (min).

*$P < 0.05$ vs. 0 μM CORM-2 of same condition;

†$P < 0.05$ vs. undiluted plasma with same concentration of CORM-2;

‡$P < 0.05$ vs. 30% NS with the same concentration of CORM-2.

Discussion

CORM-2 exposure enhanced coagulation and diminished fibrinolytic vulnerability in undiluted and diluted plasma thrombi. Equivalent dilution with NS resulted in faster forming, stronger, longer lasting thrombi than those observed with HES dilution. Supranormal to normal coagulation kinetics and fibrinolytic resistance was maintained by CORM-2 exposure in plasma following up to 40% dilution with NS, but as little as 20% dilution with VOL degraded clot growth-disintegration kinetics despite the presence of CORM-2.

What is claimed is:

1. A method for enhancing coagulation or reducing fibrinolysis in a subject, comprising:
   a) selecting a subject in need of enhanced coagulation or reduced fibrinolysis; and
   b) administering to the subject a carbon monoxide releasing molecule (CORM).

2. The method of claim 1, wherein the CORM is a tricarbonyldichlororuthenium (II) dimer.

3. The method of claim 1, wherein the CORM is selected from the group consisting of tricarbonylchloro(glycinato)ruthenium (II), sodium boranocarbonate, dimanganese decacarbonyl, and iron pentacarbonyl.

4. The method of claim 1, wherein a single dose of the CORM is administered to the subject.

5. The method of claim 4, wherein the dose comprises 25 μM to 200 μM of the CORM.

6. The method of claim 1, wherein the CORM is administered at or near a site of bleeding.

7. The method of claim 1, wherein the CORM is administered topically, by local injection, intravenously, or intramuscularly.

8. The method of claim 1, wherein the CORM is formulated for administration by an aerosol spray, an ointment, a bandage, a surgical dressing, a wound packing, a swab, a liquid, a paste, a cream, a lotion, a foam, a gel, an emulsion, a powder, dental floss, a dental instrument, or a needle.

9. The method of claim 1, wherein the CORM is co-administered with a hemostatic agent, a coagulant, an anti-fibrinolytic medication, a blood coagulation factor, fibrin, thrombin, recombinant activated factor VII, prothrombin complex concentrate, FEIBA, or a therapeutic agent selected from the group consisting of an antibiotic, an anesthetic, an analgesic, an antihistamine, an antimicrobial, an antifungal, an antiviral, and an anti-inflammatory agent.

10. The method of claim 9, wherein the blood coagulation factor is factor VIII, factor IX, factor XIII, or von Willebrand's factor.

11. The method of claim 1, wherein the subject has a disease or condition associated with bleeding.

12. The method of claim 11, wherein the disease or condition associated with bleeding is hemophilia, thrombocytopenia, von Willebrand disease, hereditary hemorrhagic telangiectasia, disseminated intravascular coagulation, or an open wound.

13. The method of claim 12, wherein the open wound is caused by trauma or injury or is due to a surgical procedure.

14. The method of claim 1, wherein the subject is undergoing surgery or hemodilution.

15. The method of claim 1, wherein the subject is in need of increased blood clot formation.

16. The method of claim 15, wherein the subject is being treated with an anticoagulant, an antiplatelet medication, an anti-thrombin, or a fibrinolytic medication.

\* \* \* \* \*